US012594251B2

(12) United States Patent
McCormick et al.

(10) Patent No.: US 12,594,251 B2
(45) Date of Patent: Apr. 7, 2026

(54) BENZALKONIUM CHLORIDE FORUSE IN TREATING CONJUNCTIVITIS AND/OR COVID-19

(71) Applicant: BAUSCH + LOMB IRELAND LIMITED, Dublin (IE)

(72) Inventors: Patrick McCormick, Rochester, NY (US); Kimberly Millard, Rochester, NY (US)

(73) Assignee: Bausch + Lomb Ireland Limited, Dublin (IE)

( * ) Notice: Subject to any disclaimer, the term of this patent is extended or adjusted under 35 U.S.C. 154(b) by 417 days.

(21) Appl. No.: 18/248,841

(22) PCT Filed: Oct. 14, 2021

(86) PCT No.: PCT/IB2021/059468

§ 371 (c)(1),
(2) Date: Apr. 12, 2023

(87) PCT Pub. No.: WO2022/079664

PCT Pub. Date: Apr. 21, 2022

(65) Prior Publication Data

US 2023/0390219 A1 Dec. 7, 2023

Related U.S. Application Data

(60) Provisional application No. 63/092,399, filed on Oct. 15, 2020, provisional application No. 63/183,928, filed on May 4, 2021, provisional application No. 63/226,614, filed on Jul. 28, 2021.

(51) Int. Cl.

| | |
|---|---|
| ***A61K 31/14*** | (2006.01) |
| ***A61K 9/00*** | (2006.01) |
| ***A61K 9/08*** | (2006.01) |
| ***A61K 31/4402*** | (2006.01) |
| ***A61K 31/498*** | (2006.01) |
| ***A61K 31/55*** | (2006.01) |
| ***A61P 31/14*** | (2006.01) |

(52) U.S. Cl.

CPC ............ *A61K 31/14* (2013.01); *A61K 9/0048* (2013.01); *A61K 9/08* (2013.01); *A61K 31/4402* (2013.01); *A61K 31/498* (2013.01); *A61K 31/55* (2013.01); *A61P 31/14* (2018.01)

(58) Field of Classification Search

CPC ........... A61K 31/14; A61P 27/02; A61P 31/14
USPC ......................................................... 514/643
See application file for complete search history.

(56) References Cited

FOREIGN PATENT DOCUMENTS

| | | | | |
|---|---|---|---|---|
| CN | 111 494 452 A * | 8/2020 | ........... A61K 31/191 |
| EP | 3936132 A1 | 1/2022 | |
| WO | WO 2011/116020 A2 | 9/2011 | |
| WO | WO 2021/195580 A1 | 9/2021 | |
| WO | WO 2021/211808 A1 | 10/2021 | |
| WO | WO 2021/216118 A1 | 10/2021 | |

OTHER PUBLICATIONS

Romanowski, E.G. et al.: Benzylkonium chloride demonstrates concentration-dependent antiviral activity against adenovirus in vitro. Journal of Ocular Pharmacology and Therapeutics, vo. 35, pp. 311-314, 2019.*

Shrank, C.L. et al.: Are quaternary ammonium compounds, the workhorse disinfectants, effective against severe acute respiratory syndrome coronavirus-2? Vo. 8, pp. 1553-1557, 2020.*

International Preliminary Report on Patentability in PCT/IB2021/059468, 10 pages (Apr. 13, 2023).

Schrank et al., "Are Quaternary Ammonium Compounds, the Workhorse Disinfectants, Effective Against Severe Acute Respiratory Syndrome-Coronavirus-2?," *ACS Infectious Diseases,* vol. 6, No. 7 (Jul. 10, 2020).

Romanowski et al., "Benzalkonium Chloride Demonstrates Concentration-Dependent Antiviral Activity Against Adenovirus In Vitro," Journal of Ocular Pharmacology and Therapeutics, vol. 35, No. 5 (Jun. 1, 2019).

Ogilvie et al., "Alcohol-Free Sanitizer and Other Quaternary Ammonium Disinfectants Quickly and Effectively Inactivate SARS-COV-2," *Journal of Hospital Infection,* vol. 108 (Nov. 28, 2020).

Anonymous, "Neue Wissenschaftliche Studie Zeigt: Dorithricin Kann SARS-COV-2 Inaktivieren" (Aug. 25, 2021).

Schütz et al., "Carrageenan-Containing Over-the-Counter Nasal and Oral Sprays Inhibit SARS-COV-2 Infection of Airway Epithelial Cultures," *American Journal of Physiology—Lung Cellular and Molecular Physiology*, vol. 320, No. 5 (Feb. 9, 2021).

Baldas, "Ann Arbor Company Says its Nasal Antiseptic Can Kill Coronavirus" (May 12, 2020).

Hilton, "Questions Raised Over Anti-Viral Nasal Protection" (Jun. 23, 2020).

Pannu et al., "Nanodroplet-Benzalkonium Chloride Formulation Demonstrates In Vitro and Ex-Vivo Broad- Spectrum Antiviral Activity Against SARS-COV-2 and Other Enveloped Viruses" (Nov. 12, 2020).

Konrat et al., "The Anti-Histamine Azelastine, Identified by Computational Drug Repurposing, Inhibits SARS-COV-2 Infection in Reconstituted Human Nasal Tissue In Vitro" (Sep. 15, 2020).

* cited by examiner

*Primary Examiner* — Charanjit Aulakh
(74) *Attorney, Agent, or Firm* — Finnegan, Henderson, Farabow, Garrett & Dunner, LLP

(57) ABSTRACT

Methods for treating coronavirus disease 2019 (COVID-19), including at least one ocular manifestation of COVID-19, methods for treating conjunctivitis, and methods for reducing COVID-19 transmission comprising administering an effective amount of benzalkonium chloride are disclosed. Pharmaceutical compositions comprising benzalkonium chloride are also disclosed.

40 Claims, No Drawings

BENZALKONIUM CHLORIDE FORUSE IN TREATING CONJUNCTIVITIS AND/OR COVID-19

CROSS-REFERENCE TO RELATED APPLICATION

This is a United States National Stage entry under 35 U.S.C. § 371 of International Patent Application No. PCT/IB2021/059468, filed Oct. 14, 2021, which claims the benefit of priority of U.S. Provisional Application Nos. 63/092,399, filed Oct. 15, 2020; 63/183,928, filed May 4, 2021; and 63/226,614, filed Jul. 28, 2021, the contents of each of which are incorporated herein by reference in their entireties.

This application claims the benefit of priority of U.S. Provisional Patent Application No. 63/092,399, filed Oct. 15, 2020, U.S. Provisional Patent Application No. 63/183,928, filed May 4, 2021, and U.S. Provisional Patent Application No. 63/226,614, filed Jul. 28, 2021, the contents of each of which are incorporated by reference herein in their entirety.

Disclosed herein are methods for treating conjunctivitis and/or coronavirus disease 2019 (COVID-19), including at least one ocular manifestation of COVID-19, using benzalkonium chloride, as well as methods for reducing COVID-19 transmission, including ocular transmission of COVID-19, using the same. Pharmaceutical compositions comprising benzalkonium chloride are also disclosed.

Coronavirus disease 2019 (COVID-19) is an infectious disease caused by severe acute respiratory syndrome coronavirus 2 (SARS-CoV-2). SARS-CoV-2 appears to be transmitted through direct or indirect contact with mucosal surfaces, such as, e.g., the nose, mouth, and/or ocular surface. Ocular surface cells, including corneal and conjunctival epithelia cells, express the receptors angiotensin I-converting enzyme 2 (ACE2) and cluster of differentiation 147 (CD147), as well as the transmembrane protease serine 2 (TMPRSS2), all of which have been implicated in SARS-CoV-2 host cell invasion.

While symptomatic COVID-19 patients typically exhibit fever, respiratory symptoms (such as, e.g., coughing), and/or fatigue, extra-pulmonary manifestations (such as, e.g., ocular manifestations) of the disease have been reported. Illustratively, SARS-CoV-2 has been identified in the tears and ocular secretions of some COVID-19 patients, and ocular infection by SARS-CoV-2 may result in eye conditions and disorders, such as, e.g., eye redness, conjunctivitis, keratoconjunctivitis, dry eye disease, blurred vision, conjunctival hyperaemia, ocular irritation, foreign body sensation, epiphora, eyelid edema, and/or chemosis. Additionally, virus on the ocular surface may be transmitted to the respiratory tract via the nasolacrimal ducts, exacerbating pulmonary symptoms of COVID-19. Accordingly, there is a need for novel prophylactics and treatments for COVID-19, including prophylactics and treatments for COVID-19-related ocular conditions and disorders.

Benzalkonium chloride (BAK) is a mixture of quaternary ammonium compounds of the following structure, wherein n is 8, 10, 12, 14, 16, or 18:

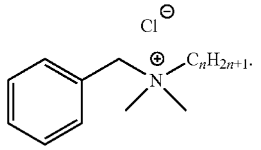

BAK is a cationic surfactant and antimicrobial agent commonly used as a preservative in ophthalmic topical solutions. Typical BAK concentrations in ophthalmic topical solutions range from 0.001% (w/v) to 0.02% (w/v), such as, e.g., from 0.004% (w/v) to 0.02% (w/v).

Disclosed herein are methods for treating at least one ocular manifestation of coronavirus disease 2019 (COVID-19) comprising administering to a subject in need thereof an effective amount of benzalkonium chloride.

In some embodiments, the effective amount of benzalkonium chloride is administered in the form of a drug delivery vehicle (such as, e.g., a dispersed system, a liposomal composition, or a micellar composition).

In some embodiments, the effective amount of benzalkonium chloride is administered in the form of a dispersed system. In some embodiments, the effective amount of benzalkonium chloride is administered in the form of a submicron dispersed system. In some embodiments, the effective amount of benzalkonium chloride is administered in the form of a submicron dispersed system chosen from submicron emulsions, aqueous lecithin dispersions, aqueous polysorbate 80 dispersions, and nanosphere suspensions. In some embodiments, the effective amount of benzalkonium chloride is administered in a submicron dispersed system described in Watrobska-Swietlikowska, *AAPS PharmSciTech,* 21:7 (2020), DOI: 10.1208/s12249-019-1540-7, which is incorporated by reference herein.

In some embodiments, the effective amount of benzalkonium chloride is administered in the form of a liposomal composition. In some embodiments, the effective amount of benzalkonium chloride is administered in the form of a liposomal composition, wherein at least some liposomes in the liposomal composition comprise benzalkonium chloride. In some embodiments, benzalkonium chloride is sequestered within the aqueous compartment of a liposome. In some embodiments, benzalkonium chloride is sequestered within a liposomal membrane.

In some embodiments, the liposomal composition is a liposome aqueous suspension. In some embodiments, the liposomal composition comprises neutral liposomes. Liposomal compositions, which may further comprise at least one additional constituent (such as, e.g., phosphatidylcholine (PC), cholesterol, and/or lipid-conjugated hydrophilic polymers) have been explored for use in ophthalmic drug delivery applications as described in Mishra et al., *J. Drug Delivery*, Vol. 2011, Article ID 863734, DOI:10.1155/2011/863734, which is incorporated by reference herein.

Additionally, liposome aqueous suspensions comprising benzalkonium chloride have been described in U.S. Pat. No. 5,565,213, which is incorporated by reference herein. In some embodiments, the effective amount of benzalkonium chloride is administered in the form of a liposomal composition described in U.S. Pat. No. 5,565,213.

In some embodiments, the effective amount of benzalkonium chloride is administered in the form of a micellar composition. In some embodiments, the effective amount of benzalkonium chloride is administered in the form of a micellar composition, wherein at least some micelles in the micellar composition comprise benzalkonium chloride.

In some embodiments, the effective amount of benzalkonium chloride is administered in the form of a pharmaceutical composition. In some embodiments, the effective amount of benzalkonium chloride is administered in the form of a pharmaceutical composition every 6 to 8 hours. In some embodiments, the effective amount of benzalkonium chloride is administered in the form of a pharmaceutical composition every 8 hours.

In some embodiments, the effective amount of benzalkonium chloride is administered in the form of a pharmaceutical composition comprising 0.001% (w/v) to 0.02% (w/v) benzalkonium chloride. In some embodiments, the effective amount of benzalkonium chloride is administered in the form of a pharmaceutical composition comprising 0.01% (w/v) benzalkonium chloride. In some embodiments, the pharmaceutical composition is chosen from Lumify®, Besivance®, and Opcon-A®.

In some embodiments, the pharmaceutical composition further comprises an effective amount of at least one additional therapeutic agent. In some embodiments, the at least one additional therapeutic agent is chosen from anti-histamines. In some embodiments, the at least one additional therapeutic agent is chosen from pheniramine maleate, carbinoxamine maleate, S-(+)-chlorpheniramine maleate, diphenhydramine, hydroxyzine, and azelastine. In some embodiments, the at least one additional therapeutic agent is pheniramine maleate. In some embodiments, the at least one additional therapeutic agent is chosen from anti-histamines, anti-inflammatory agents, and antibiotics. In some embodiments, the at least one additional therapeutic agent is chosen from anti-inflammatory agents and antibiotics. In some embodiments, the at least one additional therapeutic agent is chosen from fluoroquinolones and $\alpha_2$-adrenergic agonists. In some embodiments, the at least one additional therapeutic agent is chosen from besifloxacin and brimonidine tartrate.

In some embodiments, the pharmaceutical composition is the form of an eye drop, a suspension, a gel, an ointment, an injectable solution, or a spray.

In some embodiments, the effective amount of benzalkonium chloride is topically administered. In some embodiments, the effective amount of benzalkonium chloride is administered to at least one eye of a subject. In some embodiments, the effective amount of benzalkonium chloride is topically administered to at least one eye of a subject. In some embodiments, the effective amount of benzalkonium chloride is topically administered to one eye of a subject. In some embodiments, the effective amount of benzalkonium chloride is topically administered to both eyes of a subject.

In some embodiments, the methods comprise administering an effective amount of benzalkonium chloride in combination with an effective amount of at least one additional therapeutic agent. In some embodiments, the at least one additional therapeutic agent is chosen from anti-histamines. In some embodiments, the at least one additional therapeutic agent is chosen from pheniramine maleate, carbinoxamine maleate, S-(+)-chlorpheniramine maleate, diphenhydramine, hydroxyzine, and azelastine. In some embodiments, the at least one additional therapeutic agent is pheniramine maleate. In some embodiments, the at least one additional therapeutic agent is chosen from anti-histamines, anti-inflammatory agents, and antibiotics. In some embodiments, the at least one additional therapeutic agent is chosen from anti-inflammatory agents and antibiotics. In some embodiments, the at least one additional therapeutic agent is chosen from fluoroquinolones and $\alpha_2$-adrenergic agonists. In some embodiments, the at least one additional therapeutic agent is chosen from besifloxacin and brimonidine tartrate.

In some embodiments, treating at least one ocular manifestation of COVID-19 comprises treating at least one disease or condition chosen from eye redness, conjunctivitis, keratoconjunctivitis, dry eye disease, blurred vision, conjunctival hyperaemia, ocular irritation, foreign body sensation, epiphora, eyelid edema, and chemosis. In some embodiments, treating at least one ocular manifestation of COVID-19 comprises treating conjunctivitis. In some embodiments, treating at least one ocular manifestation of COVID-19 comprises improving visual acuity. In some embodiments, treating at least one ocular manifestation of COVID-19 comprises reducing eye redness, ocular irritation, or foreign body sensation.

Also disclosed herein are methods for reducing a risk of SARS-CoV-2 ocular transmission comprising administering to a subject in need thereof an effective amount of benzalkonium chloride.

In some embodiments, the effective amount of benzalkonium chloride is administered in the form of a drug delivery vehicle (such as, e.g., a dispersed system, a liposomal composition, or a micellar composition).

In some embodiments, the effective amount of benzalkonium chloride is administered in the form of a dispersed system. In some embodiments, the effective amount of benzalkonium chloride is administered in the form of a submicron dispersed system. In some embodiments, the effective amount of benzalkonium chloride is administered in the form of a submicron dispersed system chosen from submicron emulsions, aqueous lecithin dispersions, aqueous polysorbate 80 dispersions, and nanosphere suspensions. In some embodiments, the effective amount of benzalkonium chloride is administered in the form of a submicron dispersed system described in Watrobska-Swietlikowska, *AAPS PharmSciTech,* 21:7 (2020), DOI: 10.1208/s12249-019-1540-7, which is incorporated by reference herein.

In some embodiments, the effective amount of benzalkonium chloride is administered in the form of a liposomal composition. In some embodiments, the effective amount of benzalkonium chloride is administered in the form of a liposomal composition, wherein at least some liposomes in the liposomal composition comprise benzalkonium chloride. In some embodiments, benzalkonium chloride is sequestered within the aqueous compartment of a liposome. In some embodiments, benzalkonium chloride is sequestered within a liposomal membrane.

In some embodiments, at least some liposomes in the liposomal composition are targeted liposomes. In some embodiments, the targeted liposomes are targeted to at least one part of the eye. In some embodiments, the targeted liposomes comprise at least one ligand chosen from intercalating ligands and covalently coupling ligands (such as, e.g., antibodies and lectins). Targeted liposomes are known in the art and described, for example, in Kelly et al., *J. Drug Delivery,* 2011:727241 (2011); Wijetunge et al., *ACS Appl. Bio Mater.* 1(5): 1487-1495 (2018); Mishra et al., *J. Drug Delivery*, DOI:10.1155/2011/863734; and Agarwal et al., *Drug Delivery,* 23:4, 1075-1091, DOI:10.3109/10717544.2014.943336.

In some embodiments, the liposomal composition is a liposome aqueous suspension. In some embodiments, the liposomal composition comprises neutral liposomes. Liposomal compositions, which may further comprise at least one additional constituent (such as, e.g., phosphatidylcholine (PC), cholesterol, and/or lipid-conjugated hydrophilic polymers) have been explored for use in ophthalmic drug delivery applications as described in Mishra et al., *J. Drug Delivery*, Vol. 2011, Article ID 863734, DOI:10.1155/2011/863734, which is incorporated by reference herein. Additionally, liposome aqueous suspensions comprising benzalkonium chloride have been described in U.S. Pat. No. 5,565,213, which is incorporated by reference herein. In some embodiments, the effective amount of benzalkonium chloride is administered in the form of a liposomal composition described in U.S. Pat. No. 5,565,213.

In some embodiments, the effective amount of benzalkonium chloride is administered in the form of a micellar composition. In some embodiments, the effective amount of benzalkonium chloride is administered in the form of a micellar composition, wherein at least some micelles in the micellar composition comprise benzalkonium chloride.

In some embodiments, the effective amount of benzalkonium chloride is administered in the form of a pharmaceutical composition. In some embodiments, the effective amount of benzalkonium chloride is administered in the form of a pharmaceutical composition every 6 to 8 hours. In some embodiments, the effective amount of benzalkonium chloride is administered in the form of a pharmaceutical composition every 8 hours.

In some embodiments, the effective amount of benzalkonium chloride is administered in the form of a pharmaceutical composition comprising 0.001% (w/v) to 0.02% (w/v) benzalkonium chloride. In some embodiments, the effective amount of benzalkonium chloride is administered in the form of a pharmaceutical composition comprising 0.01% (w/v) benzalkonium chloride. In some embodiments, the pharmaceutical composition is chosen from Lumify®, Besivance®, and Opcon-A®.

In some embodiments, the pharmaceutical composition further comprises an effective amount of at least one additional therapeutic agent. In some embodiments, the at least one additional therapeutic agent is chosen from anti-histamines. In some embodiments, the at least one additional therapeutic agent is chosen from pheniramine maleate, carbinoxamine maleate, S-(+)-chlorpheniramine maleate, diphenhydramine, hydroxyzine, and azelastine. In some embodiments, the at least one additional therapeutic agent is pheniramine maleate. In some embodiments, the at least one additional therapeutic agent is chosen from anti-histamines, anti-inflammatory agents, and antibiotics. In some embodiments, the at least one additional therapeutic agent is chosen from anti-inflammatory agents and antibiotics. In some embodiments, the at least one additional therapeutic agent is chosen from fluoroquinolones and $\alpha_2$-adrenergic agonists. In some embodiments, the at least one additional therapeutic agent is chosen from besifloxacin and brimonidine tartrate.

In some embodiments, the pharmaceutical composition is the form of an eye drop, a suspension, a gel, an ointment, an injectable solution, or a spray.

In some embodiments, the effective amount of benzalkonium chloride is topically administered. In some embodiments, the effective amount of benzalkonium chloride is administered to at least one eye of a subject. In some embodiments, the effective amount of benzalkonium chloride is topically administered to at least one eye of a subject. In some embodiments, the effective amount of benzalkonium chloride is topically administered to one eye of a subject. In some embodiments, the effective amount of benzalkonium chloride is topically administered to both eyes of a subject.

In some embodiments, the methods comprise administering an effective amount of benzalkonium chloride in combination with an effective amount of at least one additional therapeutic agent. In some embodiments, the at least one additional therapeutic agent is chosen from anti-histamines. In some embodiments, the at least one additional therapeutic agent is chosen from pheniramine maleate, carbinoxamine maleate, S-(+)-chlorpheniramine maleate, diphenhydramine, hydroxyzine, and azelastine. In some embodiments, the at least one additional therapeutic agent is pheniramine maleate. In some embodiments, the at least one additional therapeutic agent is chosen from anti-histamines, anti-inflammatory agents, and antibiotics. In some embodiments, the at least one additional therapeutic agent is chosen from anti-inflammatory agents and antibiotics. In some embodiments, the at least one additional therapeutic agent is chosen from fluoroquinolones and $\alpha_2$-adrenergic agonists. In some embodiments, the at least one additional therapeutic agent is chosen from besifloxacin and brimonidine tartrate.

Also disclosed herein are methods for preventing coronavirus disease 2019 (COVID-19) comprising administering to a subject in need thereof an effective amount of benzalkonium chloride.

In some embodiments, the effective amount of benzalkonium chloride is administered in the form of a drug delivery vehicle (such as, e.g., a dispersed system, a liposomal composition, or a micellar composition).

In some embodiments, the effective amount of benzalkonium chloride is administered in the form of a dispersed system. In some embodiments, the effective amount of benzalkonium chloride is administered in the form of a submicron dispersed system. In some embodiments, the effective amount of benzalkonium chloride is administered in the form of a submicron dispersed system chosen from submicron emulsions, aqueous lecithin dispersions, aqueous polysorbate 80 dispersions, and nanosphere suspensions. In some embodiments, the effective amount of benzalkonium chloride is administered in the form of a submicron dispersed system described in Watrobska-Swietlikowska, *AAPS PharmSciTech,* 21:7 (2020), DOI: 10.1208/s12249-019-1540-7, which is incorporated by reference herein.

In some embodiments, the effective amount of benzalkonium chloride is administered in the form of a liposomal composition. In some embodiments, the effective amount of benzalkonium chloride is administered in the form of a liposomal composition, wherein at least some liposomes in the liposomal composition comprise benzalkonium chloride. In some embodiments, benzalkonium chloride is sequestered within the aqueous compartment of a liposome. In some embodiments, benzalkonium chloride is sequestered within a liposomal membrane.

In some embodiments, at least some liposomes in the liposomal composition are targeted liposomes. In some embodiments, the targeted liposomes are targeted to at least one part of the eye. In some embodiments, the targeted liposomes comprise at least one ligand chosen from intercalating ligands and covalently coupling ligands (such as, e.g., antibodies and lectins). Targeted liposomes are known in the art and described, for example, in Kelly et al., *J. Drug Delivery,* 2011:727241 (2011); Wijetunge et al., *ACS Appl. Bio Mater.* 1(5): 1487-1495 (2018); Mishra et al., *J. Drug Delivery*, DOI:10.1155/2011/863734; and Agarwal et al., *Drug Delivery,* 23:4, 1075-1091, DOI:10.3109/10717544.2014.943336.

In some embodiments, the liposomal composition is a liposome aqueous suspension. In some embodiments, the liposomal composition comprises neutral liposomes. In some embodiments, the liposomal composition comprises positively charged liposomes. In some embodiments, the liposomal composition comprises negatively charged liposomes. Liposomal compositions, which may further comprise at least one additional constituent (such as, e.g., phosphatidylcholine (PC), cholesterol, and/or lipid-conjugated hydrophilic polymers) have been explored for use in ophthalmic drug delivery applications as described in Mishra et al., *J. Drug Delivery*, Vol. 2011, Article ID 863734, DOI:10.1155/2011/863734, which is incorporated by reference herein. Additionally, liposome aqueous suspensions comprising benzalkonium chloride have been described in U.S. Pat. No. 5,565,213, which is incorporated by reference herein. In some embodiments, the effective amount of benzalkonium chloride is administered in the form of a liposomal composition described in U.S. Pat. No. 5,565,213.

In some embodiments, the effective amount of benzalkonium chloride is administered in the form of a micellar composition. In some embodiments, the effective amount of benzalkonium chloride is administered in the form of a micellar composition, wherein at least some micelles in the micellar composition comprise benzalkonium chloride.

In some embodiments, the effective amount of benzalkonium chloride is administered in the form of a pharmaceutical composition. In some embodiments, the effective amount of benzalkonium chloride is administered in the form of a pharmaceutical composition every 6 to 8 hours. In some embodiments, the effective amount of benzalkonium chloride is administered in the form of a pharmaceutical composition every 8 hours.

In some embodiments, the effective amount of benzalkonium chloride is administered in the form of a pharmaceutical composition comprising 0.001% (w/v) to 0.02% (w/v) benzalkonium chloride. In some embodiments, the effective amount of benzalkonium chloride is administered in the form of a pharmaceutical composition comprising 0.01% (w/v) benzalkonium chloride. In some embodiments, the pharmaceutical composition is chosen from Lumify®, Besivance®, and Opcon-A®.

In some embodiments, the pharmaceutical composition further comprises an effective amount of at least one additional therapeutic agent. In some embodiments, the at least one additional therapeutic agent is chosen from anti-histamines. In some embodiments, the at least one additional therapeutic agent is chosen from pheniramine maleate, carbinoxamine maleate, S-(+)-chlorpheniramine maleate, diphenhydramine, hydroxyzine, and azelastine. In some embodiments, the at least one additional therapeutic agent is pheniramine maleate. In some embodiments, the at least one additional therapeutic agent is chosen from anti-histamines, anti-inflammatory agents, and antibiotics. In some embodiments, the at least one additional therapeutic agent is chosen from anti-inflammatory agents and antibiotics. In some embodiments, the at least one additional therapeutic agent is chosen from fluoroquinolones and $\alpha_2$-adrenergic agonists. In some embodiments, the at least one additional therapeutic agent is chosen from besifloxacin and brimonidine tartrate.

In some embodiments, the pharmaceutical composition is the form of an eye drop, a suspension, a gel, an ointment, an injectable solution, or a spray.

In some embodiments, the effective amount of benzalkonium chloride is topically administered. In some embodiments, the effective amount of benzalkonium chloride is administered to at least one eye of a subject. In some embodiments, the effective amount of benzalkonium chloride is topically administered to at least one eye of a subject. In some embodiments, the effective amount of benzalkonium chloride is topically administered to one eye of a subject. In some embodiments, the effective amount of benzalkonium chloride is topically administered to both eyes of a subject.

In some embodiments, the methods comprise administering an effective amount of benzalkonium chloride in combination with an effective amount of at least one additional therapeutic agent. In some embodiments, the at least one additional therapeutic agent is chosen from anti-histamines. In some embodiments, the at least one additional therapeutic agent is chosen from pheniramine maleate, carbinoxamine maleate, S-(+)-chlorpheniramine maleate, diphenhydramine, hydroxyzine, and azelastine. In some embodiments, the at least one additional therapeutic agent is pheniramine maleate. In some embodiments, the at least one additional therapeutic agent is chosen from anti-histamines, anti-inflammatory agents, and antibiotics. In some embodiments, the at least one additional therapeutic agent is chosen from anti-inflammatory agents and antibiotics. In some embodiments, the at least one additional therapeutic agent is chosen from fluoroquinolones and $\alpha_2$-adrenergic agonists. In some embodiments, the at least one additional therapeutic agent is chosen from besifloxacin and brimonidine tartrate.

In some embodiments, preventing COVID-19 comprises preventing at least one ocular manifestation of COVID-19.

Also disclosed herein are methods for reducing an ocular SARS-CoV-2 viral load comprising administering to a subject in need thereof an effective amount of benzalkonium chloride.

In some embodiments, the effective amount of benzalkonium chloride is administered in the form of a drug delivery vehicle (such as, e.g., a dispersed system, a liposomal composition, or a micellar composition).

In some embodiments, the effective amount of benzalkonium chloride is administered in the form of a dispersed system. In some embodiments, the effective amount of benzalkonium chloride is administered in the form of a submicron dispersed system. In some embodiments, the effective amount of benzalkonium chloride is administered in the form of a submicron dispersed system chosen from submicron emulsions, aqueous lecithin dispersions, aqueous polysorbate 80 dispersions, and nanosphere suspensions. In some embodiments, the effective amount of benzalkonium chloride is administered in the form of a submicron dispersed system described in Watrobska-Swietlikowska, *AAPS PharmSciTech,* 21:7 (2020), DOI: 10.1208/s12249-019-1540-7, which is incorporated by reference herein.

In some embodiments, the effective amount of benzalkonium chloride is administered in the form of a liposomal composition. In some embodiments, the effective amount of benzalkonium chloride is administered in the form of a liposomal composition, wherein at least some liposomes in the liposomal composition comprise benzalkonium chloride. In some embodiments, benzalkonium chloride is sequestered within the aqueous compartment of a liposome. In some embodiments, benzalkonium chloride is sequestered within a liposomal membrane.

In some embodiments, at least some liposomes in the liposomal composition are targeted liposomes. In some embodiments, the targeted liposomes are targeted to at least one part of the eye. In some embodiments, the targeted liposomes comprise at least one ligand chosen from intercalating ligands and covalently coupling ligands (such as, e.g., antibodies and lectins). Targeted liposomes are known in the art and described, for example, in Kelly et al., *J. Drug Delivery,* 2011:727241 (2011); Wijetunge et al., *ACS Appl. Bio Mater.* 1(5): 1487-1495 (2018); Mishra et al., *J. Drug Delivery*, DOI:10.1155/2011/863734; and Agarwal et al., *Drug Delivery,* 23:4, 1075-1091, DOI:10.3109/10717544.2014.943336.

In some embodiments, the liposomal composition is a liposome aqueous suspension. In some embodiments, the liposomal composition comprises neutral liposomes. In some embodiments, the liposomal composition comprises positively charged liposomes. In some embodiments, the liposomal composition comprises negatively charged liposomes. Liposomal compositions, which may further comprise at least one additional constituent (such as, e.g., phosphatidylcholine (PC), cholesterol, and/or lipid-conjugated hydrophilic polymers) have been explored for use in ophthalmic drug delivery applications as described in Mishra et al., *J. Drug Delivery*, Vol. 2011, Article ID 863734, DOI:10.1155/2011/863734, which is incorporated by reference herein. Additionally, liposome aqueous suspensions comprising benzalkonium chloride have been described in U.S. Pat. No. 5,565,213, which is incorporated by reference herein. In some embodiments, the effective amount of benzalkonium chloride is administered in the form of a liposomal composition described in U.S. Pat. No. 5,565,213.

In some embodiments, the effective amount of benzalkonium chloride is administered in the form of a micellar composition. In some embodiments, the effective amount of benzalkonium chloride is administered in the form of a micellar composition, wherein at least some micelles in the micellar composition comprise benzalkonium chloride.

In some embodiments, the effective amount of benzalkonium chloride is administered in the form of a pharmaceutical composition. In some embodiments, the effective amount of benzalkonium chloride is administered in the form of a pharmaceutical composition every 6 to 8 hours. In some embodiments, the effective amount of benzalkonium chloride is administered in the form of a pharmaceutical composition every 8 hours.

In some embodiments, the effective amount of benzalkonium chloride is administered in the form of a pharmaceutical composition comprising 0.001% (w/v) to 0.02% (w/v) benzalkonium chloride. In some embodiments, the effective amount of benzalkonium chloride is administered in the form of a pharmaceutical composition comprising 0.01% (w/v) benzalkonium chloride. In some embodiments, the pharmaceutical composition is chosen from Lumify®, Besivance®, and Opcon-A®.

In some embodiments, the pharmaceutical composition further comprises an effective amount of at least one additional therapeutic agent. In some embodiments, the at least one additional therapeutic agent is chosen from anti-histamines. In some embodiments, the at least one additional therapeutic agent is chosen from pheniramine maleate, carbinoxamine maleate, S-(+)-chlorpheniramine maleate, diphenhydramine, hydroxyzine, and azelastine. In some embodiments, the at least one additional therapeutic agent is pheniramine maleate. In some embodiments, the at least one additional therapeutic agent is chosen from anti-histamines, anti-inflammatory agents, and antibiotics. In some embodiments, the at least one additional therapeutic agent is chosen from anti-inflammatory agents and antibiotics. In some embodiments, the at least one additional therapeutic agent is chosen from fluoroquinolones and $\alpha_2$-adrenergic agonists. In some embodiments, the at least one additional therapeutic agent is chosen from besifloxacin and brimonidine tartrate.

In some embodiments, the pharmaceutical composition is the form of an eye drop, a suspension, a gel, an ointment, an injectable solution, or a spray.

In some embodiments, the effective amount of benzalkonium chloride is topically administered. In some embodiments, the effective amount of benzalkonium chloride is administered to at least one eye of a subject. In some embodiments, the effective amount of benzalkonium chloride is topically administered to at least one eye of a subject. In some embodiments, the effective amount of benzalkonium chloride is topically administered to one eye of a subject. In some embodiments, the effective amount of benzalkonium chloride is topically administered to both eyes of a subject.

In some embodiments, the methods comprise administering an effective amount of benzalkonium chloride in combination with an effective amount of at least one additional therapeutic agent. In some embodiments, the at least one additional therapeutic agent is chosen from anti-histamines. In some embodiments, the at least one additional therapeutic agent is chosen from pheniramine maleate, carbinoxamine maleate, S-(+)-chlorpheniramine maleate, diphenhydramine, hydroxyzine, and azelastine. In some embodiments, the at least one additional therapeutic agent is pheniramine maleate. In some embodiments, the at least one additional therapeutic agent is chosen from anti-histamines, anti-inflammatory agents, and antibiotics. In some embodiments, the at least one additional therapeutic agent is chosen from anti-inflammatory agents and antibiotics. In some embodiments, the at least one additional therapeutic agent is chosen from fluoroquinolones and $\alpha_2$-adrenergic agonists. In some embodiments, the at least one additional therapeutic agent is chosen from besifloxacin and brimonidine tartrate.

In some embodiments, reducing an ocular SARS-CoV-2 viral load comprises reducing the ocular SARS-CoV-2 viral load by 25% compared to a pre-treatment ocular SARS-CoV-2 viral load. In some embodiments, reducing an ocular SARS-CoV-2 viral load comprises reducing the ocular SARS-CoV-2 viral load by 50% compared to a pre-treatment ocular SARS-CoV-2 viral load. In some embodiments, reducing an ocular SARS-CoV-2 viral load comprises reducing the ocular SARS-CoV-2 viral load by 75% compared to a pre-treatment ocular SARS-CoV-2 viral load.

Also disclosed herein are methods for treating conjunctivitis comprising administering to a subject in need thereof an effective amount of benzalkonium chloride.

In some embodiments, treating conjunctivitis comprises treating viral conjunctivitis. In some embodiments, treating conjunctivitis comprises treating conjunctivitis of unknown etiology.

In some embodiments, the effective amount of benzalkonium chloride is administered in the form of a drug delivery vehicle (such as, e.g., a dispersed system, a liposomal composition, or a micellar composition).

In some embodiments, the effective amount of benzalkonium chloride is administered in the form of a dispersed system. In some embodiments, the effective amount of benzalkonium chloride is administered in the form of a submicron dispersed system. In some embodiments, the effective amount of benzalkonium chloride is administered in the form of a submicron dispersed system chosen from submicron emulsions, aqueous lecithin dispersions, aqueous polysorbate 80 dispersions, and nanosphere suspensions. In some embodiments, the effective amount of benzalkonium chloride is administered in the form of a submicron dispersed system described in Watrobska-Swietlikowska, *AAPS PharmSciTech,* 21:7 (2020), DOI: 10.1208/s12249-019-1540-7, which is incorporated by reference herein.

In some embodiments, the effective amount of benzalkonium chloride is administered in the form of a liposomal composition. In some embodiments, the effective amount of benzalkonium chloride is administered in the form of a liposomal composition, wherein at least some liposomes in the liposomal composition comprise benzalkonium chloride. In some embodiments, benzalkonium chloride is sequestered within the aqueous compartment of a liposome. In some embodiments, benzalkonium chloride is sequestered within a liposomal membrane.

In some embodiments, at least some liposomes in the liposomal composition are targeted liposomes. In some embodiments, the targeted liposomes are targeted to at least one part of the eye. In some embodiments, the targeted liposomes comprise at least one ligand chosen from intercalating ligands and covalently coupling ligands (such as, e.g., antibodies and lectins). Targeted liposomes are known in the art and described, for example, in Kelly et al., *J. Drug Delivery,* 2011:727241 (2011); Wijetunge et al., *ACS Appl. Bio Mater.* 1(5): 1487-1495 (2018); Mishra et al., *J. Drug Delivery*, DOI:10.1155/2011/863734; and Agarwal et al., *Drug Delivery,* 23:4, 1075-1091, DOI:10.3109/10717544.2014.943336.

In some embodiments, the liposomal composition is a liposome aqueous suspension. In some embodiments, the liposomal composition comprises neutral liposomes. In some embodiments, the liposomal composition comprises positively charged liposomes. In some embodiments, the liposomal composition comprises negatively charged liposomes. Liposomal compositions, which may further comprise at least one additional constituent (such as, e.g., phosphatidylcholine (PC), cholesterol, and/or lipid-conjugated hydrophilic polymers) have been explored for use in ophthalmic drug delivery applications as described in Mishra et al., *J. Drug Delivery*, Vol. 2011, Article ID 863734, DOI:10.1155/2011/863734, which is incorporated by reference herein. Additionally, liposome aqueous suspensions comprising benzalkonium chloride have been described in U.S. Pat. No. 5,565,213, which is incorporated by reference herein. In some embodiments, the effective amount of benzalkonium chloride is administered in the form of a liposomal composition described in U.S. Pat. No. 5,565,213.

In some embodiments, the effective amount of benzalkonium chloride is administered in the form of a micellar composition. In some embodiments, the effective amount of benzalkonium chloride is administered in the form of a micellar composition, wherein at least some micelles in the micellar composition comprise benzalkonium chloride.

In some embodiments, the effective amount of benzalkonium chloride is administered in the form of a pharmaceutical composition. In some embodiments, the effective amount of benzalkonium chloride is administered in the form of a pharmaceutical composition every 6 to 8 hours. In some embodiments, the effective amount of benzalkonium chloride is administered in the form of a pharmaceutical composition every 8 hours.

In some embodiments, the effective amount of benzalkonium chloride is administered in the form of a pharmaceutical composition comprising 0.001% (w/v) to 0.02% (w/v) benzalkonium chloride. In some embodiments, the effective amount of benzalkonium chloride is administered in the form of a pharmaceutical composition comprising 0.01% (w/v) benzalkonium chloride. In some embodiments, the pharmaceutical composition is chosen from Lumify®, Besivance®, and Opcon-A®.

In some embodiments, the pharmaceutical composition further comprises an effective amount of at least one additional therapeutic agent. In some embodiments, the at least one additional therapeutic agent is chosen from anti-histamines. In some embodiments, the at least one additional therapeutic agent is chosen from pheniramine maleate, carbinoxamine maleate, S-(+)-chlorpheniramine maleate, diphenhydramine, hydroxyzine, and azelastine. In some embodiments, the at least one additional therapeutic agent is pheniramine maleate. In some embodiments, the at least one additional therapeutic agent is chosen from anti-histamines, anti-inflammatory agents, and antibiotics. In some embodiments, the at least one additional therapeutic agent is chosen from anti-inflammatory agents and antibiotics. In some embodiments, the at least one additional therapeutic agent is chosen from fluoroquinolones and $\alpha_2$-adrenergic agonists. In some embodiments, the at least one additional therapeutic agent is chosen from besifloxacin and brimonidine tartrate.

In some embodiments, the pharmaceutical composition is the form of an eye drop, a suspension, a gel, an ointment, an injectable solution, or a spray.

In some embodiments, the effective amount of benzalkonium chloride is topically administered. In some embodiments, the effective amount of benzalkonium chloride is administered to at least one eye of a subject. In some embodiments, the effective amount of benzalkonium chloride is topically administered to at least one eye of a subject. In some embodiments, the effective amount of benzalkonium chloride is topically administered to one eye of a subject. In some embodiments, the effective amount of benzalkonium chloride is topically administered to both eyes of a subject.

In some embodiments, the methods comprise administering an effective amount of benzalkonium chloride in combination with an effective amount of at least one additional therapeutic agent. In some embodiments, the at least one additional therapeutic agent is chosen from anti-histamines. In some embodiments, the at least one additional therapeutic agent is chosen from pheniramine maleate, carbinoxamine maleate, S-(+)-chlorpheniramine maleate, diphenhydramine, hydroxyzine, and azelastine. In some embodiments, the at least one additional therapeutic agent is pheniramine maleate. In some embodiments, the at least one additional therapeutic agent is chosen from anti-histamines, anti-inflammatory agents, and antibiotics. In some embodiments, the at least one additional therapeutic agent is chosen from anti-inflammatory agents and antibiotics. In some embodiments, the at least one additional therapeutic agent is chosen from fluoroquinolones and $\alpha_2$-adrenergic agonists. In some embodiments, the at least one additional therapeutic agent is chosen from besifloxacin and brimonidine tartrate.

Also disclosed herein are methods for preventing conjunctivitis comprising administering to a subject in need thereof an effective amount of benzalkonium chloride.

In some embodiments, the subject exhibits at least one symptom of a viral infection. In some embodiments, the subject exhibits at least one symptom of a SARS CoV-2 infection.

In some embodiments, the subject is infected with a virus. In some embodiments, the subject is infected with SARS-CoV-2.

In some embodiments, the effective amount of benzalkonium chloride is administered in the form of a drug delivery vehicle (such as, e.g., a dispersed system, a liposomal composition, or a micellar composition).

In some embodiments, the effective amount of benzalkonium chloride is administered in the form of a dispersed system. In some embodiments, the effective amount of benzalkonium chloride is administered in the form of a submicron dispersed system. In some embodiments, the effective amount of benzalkonium chloride is administered in the form of a submicron dispersed system chosen from submicron emulsions, aqueous lecithin dispersions, aqueous polysorbate 80 dispersions, and nanosphere suspensions. In some embodiments, the effective amount of benzalkonium chloride is administered in the form of a submicron dispersed system described in Watrobska-Swietlikowska, *AAPS PharmSciTech,* 21:7 (2020), DOI: 10.1208/s12249-019-1540-7, which is incorporated by reference herein.

In some embodiments, the effective amount of benzalkonium chloride is administered in the form of a liposomal composition. In some embodiments, the effective amount of benzalkonium chloride is administered in the form of a liposomal composition, wherein at least some liposomes in the liposomal composition comprise benzalkonium chloride. In some embodiments, benzalkonium chloride is sequestered within the aqueous compartment of a liposome. In some embodiments, benzalkonium chloride is sequestered within a liposomal membrane.

In some embodiments, at least some liposomes in the liposomal composition are targeted liposomes. In some embodiments, the targeted liposomes are targeted to at least one part of the eye. In some embodiments, the targeted liposomes comprise at least one ligand chosen from intercalating ligands and covalently coupling ligands (such as, e.g., antibodies and lectins). Targeted liposomes are known in the art and described, for example, in Kelly et al., *J. Drug Delivery,* 2011:727241 (2011); Wijetunge et al., *ACS Appl. Bio Mater.* 1(5): 1487-1495 (2018); Mishra et al., *J. Drug Delivery*, DOI:10.1155/2011/863734; and Agarwal et al., *Drug Delivery,* 23:4, 1075-1091, DOI:10.3109/10717544.2014.943336.

In some embodiments, the liposomal composition is a liposome aqueous suspension. In some embodiments, the liposomal composition comprises neutral liposomes. In some embodiments, the liposomal composition comprises positively charged liposomes. In some embodiments, the liposomal composition comprises negatively charged liposomes. Liposomal compositions, which may further comprise at least one additional constituent (such as, e.g., phosphatidylcholine (PC), cholesterol, and/or lipid-conjugated hydrophilic polymers) have been explored for use in ophthalmic drug delivery applications as described in Mishra et al., *J. Drug Delivery*, Vol. 2011, Article ID 863734, DOI:10.1155/2011/863734, which is incorporated by reference herein. Additionally, liposome aqueous suspensions comprising benzalkonium chloride have been described in U.S. Pat. No. 5,565,213, which is incorporated by reference herein. In some embodiments, the effective amount of benzalkonium chloride is administered in the form of a liposomal composition described in U.S. Pat. No. 5,565,213.

In some embodiments, the effective amount of benzalkonium chloride is administered in the form of a micellar composition. In some embodiments, the effective amount of benzalkonium chloride is administered in the form of a micellar composition, wherein at least some micelles in the micellar composition comprise benzalkonium chloride.

In some embodiments, the effective amount of benzalkonium chloride is administered in the form of a pharmaceutical composition.

In some embodiments, the effective amount of benzalkonium chloride is administered in the form of a pharmaceutical composition every 6 to 8 hours. In some embodiments, the effective amount of benzalkonium chloride is administered in the form of a pharmaceutical composition every 8 hours. In some embodiments, the effective amount of benzalkonium chloride is administered in the form of a pharmaceutical composition comprising 0.001% (w/v) to 0.02% (w/v) benzalkonium chloride. In some embodiments, the effective amount of benzalkonium chloride is administered in the form of a pharmaceutical composition comprising 0.01% (w/v) benzalkonium chloride. In some embodiments, the pharmaceutical composition is chosen from Lumify®, Besivance®, and Opcon-A®.

In some embodiments, the pharmaceutical composition further comprises an effective amount of at least one additional therapeutic agent. In some embodiments, the at least one additional therapeutic agent is chosen from anti-histamines. In some embodiments, the at least one additional therapeutic agent is chosen from pheniramine maleate, carbinoxamine maleate, S-(+)-chlorpheniramine maleate, diphenhydramine, hydroxyzine, and azelastine. In some embodiments, the at least one additional therapeutic agent is pheniramine maleate. In some embodiments, the at least one additional therapeutic agent is chosen from anti-histamines, anti-inflammatory agents, and antibiotics. In some embodiments, the at least one additional therapeutic agent is chosen from anti-inflammatory agents and antibiotics. In some embodiments, the at least one additional therapeutic agent is chosen from fluoroquinolones and $\alpha_2$-adrenergic agonists. In some embodiments, the at least one additional therapeutic agent is chosen from besifloxacin and brimonidine tartrate.

In some embodiments, the pharmaceutical composition is the form of an eye drop, a suspension, a gel, an ointment, an injectable solution, or a spray.

In some embodiments, the effective amount of benzalkonium chloride is topically administered. In some embodiments, the effective amount of benzalkonium chloride is administered to at least one eye of a subject. In some embodiments, the effective amount of benzalkonium chloride is topically administered to at least one eye of a subject. In some embodiments, the effective amount of benzalkonium chloride is topically administered to one eye of a subject. In some embodiments, the effective amount of benzalkonium chloride is topically administered to both eyes of a subject.

In some embodiments, the methods comprise administering an effective amount of benzalkonium chloride in combination with an effective amount of at least one additional therapeutic agent. In some embodiments, the at least one additional therapeutic agent is chosen from anti-histamines. In some embodiments, the at least one additional therapeutic agent is chosen from pheniramine maleate, carbinoxamine maleate, S-(+)-chlorpheniramine maleate, diphenhydramine, hydroxyzine, and azelastine. In some embodiments, the at least one additional therapeutic agent is pheniramine maleate. In some embodiments, the at least one additional therapeutic agent is chosen from anti-histamines, anti-inflammatory agents, and antibiotics. In some embodiments, the at least one additional therapeutic agent is chosen from anti-inflammatory agents and antibiotics. In some embodiments, the at least one additional therapeutic agent is chosen from fluoroquinolones and $\alpha_2$-adrenergic agonists. In some embodiments, the at least one additional therapeutic agent is chosen from besifloxacin and brimonidine tartrate.

Also disclosed herein are methods for reducing an intranasal SARS-CoV-2 viral load comprising administering to a subject in need thereof an effective amount of benzalkonium chloride.

In some embodiments, the effective amount of benzalkonium chloride is administered in the form of a pharmaceutical composition. In some embodiments, the effective amount of benzalkonium chloride is administered in the form of a pharmaceutical composition every 6 to 8 hours. In some embodiments, the effective amount of benzalkonium chloride is administered in the form of a pharmaceutical composition every 8 hours.

In some embodiments, the effective amount of benzalkonium chloride is administered in the form of a pharmaceutical composition comprising 0.001% (w/v) to 0.2% (w/v) benzalkonium chloride. In some embodiments, the effective amount of benzalkonium chloride is administered in the form of a pharmaceutical composition comprising 0.005% (w/v) to 0.2% (w/v) benzalkonium chloride. In some embodiments, the effective amount of benzalkonium chloride is administered in the form of a pharmaceutical composition comprising 0.005% (w/v) to 0.1% (w/v) benzalkonium chloride. In some embodiments, the effective amount of benzalkonium chloride is administered in the form of a pharmaceutical composition comprising 0.01% (w/v) benzalkonium chloride.

In some embodiments, the pharmaceutical composition further comprises an effective amount of at least one additional therapeutic agent. In some embodiments, the at least one additional therapeutic agent is chosen from anti-histamines. In some embodiments, the at least one additional therapeutic agent is chosen from pheniramine maleate, carbinoxamine maleate, S-(+)-chlorpheniramine maleate, diphenhydramine, hydroxyzine, and azelastine. In some embodiments, the at least one additional therapeutic agent is pheniramine maleate. In some embodiments, the at least one additional therapeutic agent is chosen from anti-histamines, anti-inflammatory agents, and antibiotics.

In some embodiments, the pharmaceutical composition is the form of a spray.

In some embodiments, the pharmaceutical composition is intranasally administered.

In some embodiments, the methods comprise administering an effective amount of benzalkonium chloride in combination with an effective amount of at least one additional therapeutic agent.

Also disclosed herein are methods for treating or preventing coronavirus disease 2019 (COVID-19) comprising intranasally administering to a subject in need thereof an effective amount of benzalkonium chloride.

In some embodiments, the effective amount of benzalkonium chloride is administered in the form of a drug delivery vehicle (such as, e.g., a dispersed system, a liposomal composition, or a micellar composition).

In some embodiments, the effective amount of benzalkonium chloride is administered in the form of a dispersed system. In some embodiments, the effective amount of benzalkonium chloride is administered in the form of a submicron dispersed system. In some embodiments, the effective amount of benzalkonium chloride is administered in the form of a submicron dispersed system chosen from submicron emulsions, aqueous lecithin dispersions, aqueous polysorbate 80 dispersions, and nanosphere suspensions. In some embodiments, the effective amount of benzalkonium chloride is administered in the form of a submicron dispersed system described in Watrobska-Swietlikowska, *AAPS PharmSciTech,* 21:7 (2020), DOI: 10.1208/s12249-019-1540-7, which is incorporated by reference herein.

In some embodiments, the effective amount of benzalkonium chloride is administered in the form of a liposomal composition. In some embodiments, the effective amount of benzalkonium chloride is administered in the form of a liposomal composition, wherein at least some liposomes in the liposomal composition comprise benzalkonium chloride. In some embodiments, benzalkonium chloride is sequestered within the aqueous compartment of a liposome. In some embodiments, benzalkonium chloride is sequestered within a liposomal membrane.

In some embodiments, at least some liposomes in the liposomal composition are targeted liposomes. In some embodiments, the targeted liposomes are targeted to at least one part of the eye. In some embodiments, the targeted liposomes comprise at least one ligand chosen from intercalating ligands and covalently coupling ligands (such as, e.g., antibodies and lectins). Targeted liposomes are known in the art and described, for example, in Kelly et al., *J. Drug Delivery,* 2011:727241 (2011); Wijetunge et al., *ACS Appl. Bio Mater.* 1(5): 1487-1495 (2018); Mishra et al., *J. Drug Delivery*, DOI:10.1155/2011/863734; and Agarwal et al., *Drug Delivery,* 23:4, 1075-1091, DOI:10.3109/10717544.2014.943336.

In some embodiments, the liposomal composition is a liposome aqueous suspension. In some embodiments, the liposomal composition comprises neutral liposomes. Liposomal compositions, which may further comprise at least one additionally constituent (such as, e.g., phosphatidylcholine (PC), cholesterol, and/or lipid-conjugated hydrophilic polymers) have been explored for use in ophthalmic drug delivery applications as described in Mishra et al., *J. Drug Delivery*, Vol. 2011, Article ID 863734, DOI:10.1155/2011/863734, which is incorporated by reference herein. Additionally, liposome aqueous suspensions comprising benzalkonium chloride have been described in U.S. Pat. No. 5,565,213, which is incorporated by reference herein. In some embodiments, the effective amount of benzalkonium chloride is administered in the form of a liposomal composition described in U.S. Pat. No. 5,565,213.

In some embodiments, the effective amount of benzalkonium chloride is administered in the form of a micellar composition. In some embodiments, the effective amount of benzalkonium chloride is administered in the form of a micellar composition, wherein at least some micelles in the micellar composition comprise benzalkonium chloride.

In some embodiments, the effective amount of benzalkonium chloride is intranasally administered in the form of a pharmaceutical composition.

In some embodiments, the effective amount of benzalkonium chloride is administered in the form of a pharmaceutical composition every 6 to 8 hours. In some embodiments, the effective amount of benzalkonium chloride is administered in the form of a pharmaceutical composition every 8 hours.

In some embodiments, the effective amount of benzalkonium chloride is intranasally administered in the form of a pharmaceutical composition comprising 0.001% (w/v) to 0.2% (w/v) benzalkonium chloride. In some embodiments, the effective amount of benzalkonium chloride is intranasally administered in the form of a pharmaceutical composition comprising 0.005% (w/v) to 0.2% (w/v) benzalkonium chloride. In some embodiments, the effective amount of benzalkonium chloride is intranasally administered in the form of a pharmaceutical composition comprising 0.005% (w/v) to 0.1% (w/v) benzalkonium chloride. In some embodiments, the effective amount of benzalkonium chloride is intranasally administered in the form of a pharmaceutical composition comprising 0.01% (w/v) benzalkonium chloride.

In some embodiments, the pharmaceutical composition further comprises an effective amount of at least one additional therapeutic agent. In some embodiments, the at least one additional therapeutic agent is chosen from anti-histamines. In some embodiments, the at least one additional therapeutic agent is chosen from pheniramine maleate, carbinoxamine maleate, S-(+)-chlorpheniramine maleate, diphenhydramine, hydroxyzine, and azelastine. In some embodiments, the at least one additional therapeutic agent is pheniramine maleate. In some embodiments, the at least one additional therapeutic agent is chosen from anti-histamines, anti-inflammatory agents, and antibiotics.

In some embodiments, the pharmaceutical composition is the form of a spray.

In some embodiments, the methods comprise intranasally administering an effective amount of benzalkonium chloride in combination with an effective amount of at least one additional therapeutic agent.

Definitions

As used herein, "a" or "an" entity refers to one or more of that entity, e.g., "a compound" refers to one or more compounds or at least one compound unless stated otherwise. As such, the terms "a" (or "an"), "one or more", and "at least one" are used interchangeably herein.

As used herein, the term "active pharmaceutical ingredient" or "therapeutic agent" ("API") refers to a biologically active compound.

As used herein, "administration" of an API to a patient refers to any route of introducing or delivering the API to a subject. Administration includes self-administration and the administration by another.

As used herein, a "condition," "disorder," or "disease" relates to any unhealthy or abnormal state.

As used herein, an "effective amount" or "effective dose" refers to an amount of a molecule that treats, upon single or multiple dose administration, a patient suffering from a disorder, disease, or condition. An effective amount can be determined by the attending diagnostician through the use of known techniques and by observing results obtained under analogous circumstances. In determining the effective amount, a number of factors are considered by the attending diagnostician, including, but not limited to: the species of patient; its size, age, and general health; the specific condition, disorder, or disease involved; the degree of or involvement or the severity of the condition, disorder, or disease, the response of the individual patient; the particular compound administered; the mode of administration; the bioavailability characteristics of the preparation administered; the dose regimen selected; the use of concomitant medication; and other relevant circumstances.

As used herein, the term "in combination with," when referring to two or more compounds, agents, or additional active pharmaceutical ingredients, means the administration of two or more compounds, agents, or active pharmaceutical ingredients to the patient prior to, concurrent with, or subsequent to each other during a treatment period. Unless specified otherwise, the two or more compounds, agents, or active pharmaceutical ingredients may be administered on different schedules during the treatment period, such as, e.g., with one or more compounds, agents, or active pharmaceutical ingredients being administered once a day and one or more other compounds, agents, or active pharmaceutical ingredients being administered twice a day.

As used herein, the term "increase" refers to altering positively by at least 5%, including, but not limited to, altering positively by 5%, altering positively by 10%, altering positively by 25%, altering positively by 30% altering positively by 50%, altering positively by 75%, or altering positively by 100%.

As used herein, a "mammal" refers to domesticated animals (e.g., dogs, cats, and horses) and humans. In some embodiments, the mammal is a human.

As used herein, a "manifestation" of a disorder, disease, or condition refers to a sign or symptom of the disorder, disease, or condition. For example, as used herein, a "manifestation of COVID-19" refers to a sign or symptom observed in a patient infected with SARS-CoV-2. Illustratively, an ocular manifestation of COVID-19 refers to a sign or symptom observed in one or both eyes of a patient infected with SARS-CoV-2, such as, e.g., eye redness, conjunctivitis, keratoconjunctivitis, dry eye disease, blurred vision, conjunctival hyperaemia, ocular irritation, foreign body sensation, epiphora, eyelid edema, and/or chemosis.

As used herein, the terms "patient" and "subject" are used interchangeably and refer to a mammal, such as, e.g., a human.

As used herein, "prevention" of or "preventing" a disorder, disease, or condition refers to reduction of or reducing the occurrence of the disorder, disease, or condition in a treated sample relative to an untreated control sample, and includes delaying onset, progression, or reduction of severity of one or more symptoms of the disorder or condition relative to the untreated control sample.

As used herein, a "pharmaceutically acceptable excipient" refers to a carrier or an excipient that is useful in preparing a pharmaceutical composition. For example, a pharmaceutically acceptable excipient is generally safe and includes carriers and excipients that are generally considered acceptable for mammalian pharmaceutical use. As a non-limiting example, pharmaceutically acceptable excipients may be solid, semi-solid, or liquid materials which, in the aggregate, can serve as a vehicle or medium for active ingredients. Some examples of pharmaceutically acceptable excipients are found in Remington's Pharmaceutical Sciences and the Handbook of Pharmaceutical Excipients and include diluents, vehicles, carriers, ointment bases, binders, disintegrates, lubricants, glidants, sweetening agents, flavoring agents, gel bases, sustained release matrices, stabilizing agents, preservatives, solvents, suspending agents, buffers, emulsifiers, dyes, propellants, coating agents, and others.

As used herein, the term "reduce" refers to altering negatively by at least 5% including, but not limited to, altering negatively by 5%, altering negatively by 10%, altering negatively by 25%, altering negatively by 30%, altering negatively by 50%, altering negatively by 75%, or altering negatively by 100%.

As used herein, the term "treat," "treating," or "treatment," when used in connection with a disorder or condition, includes any effect, e.g., lessening, reducing, modulating, ameliorating, or eliminating, that results in the improvement of the disorder or condition. Improvements in or lessening the severity of any symptom of the disorder or condition can be readily assessed according to standard methods and techniques known in the art.

As will be understood by one of ordinary skill in the art, each range disclosed herein includes all possible subranges as well as individual numerical values within that range, including endpoints. As a non-limiting example, a range of "0.001% to 0.02%" includes and would be understood to specifically disclose subranges such as "0.004% to 0.01%," "0.005% to 0.02%," etc., as well as all individual numbers within the disclosed range, for example, 0.001%, 0.004%, 0.005%, 0.01%, 0.02%, etc.

Claims or descriptions that include "or" or "and/or" between at least one members of a group are considered satisfied if one, more than one, or all of the group members are present in, employed in, or otherwise relevant to a given product or process unless indicated to the contrary or otherwise evident from the context. The disclosure includes embodiments in which exactly one member of the group is present in, employed in, or otherwise relevant to a given product or process. The disclosure includes embodiments in which more than one, or all the group members are present in, employed in, or otherwise relevant to a given product or process.

Some embodiments of this disclosure relate to methods for treating at least one ocular manifestation of coronavirus disease 2019 (COVID-19) comprising administering to a subject in need thereof an effective amount of benzalkonium chloride.

In some embodiments, the effective amount of benzalkonium chloride is administered in the form of a pharmaceutical composition. In some embodiments, the effective amount of benzalkonium chloride is administered in the form of a pharmaceutical composition every 6 to 8 hours. In some embodiments, the effective amount of benzalkonium chloride is administered in the form of a pharmaceutical composition every 8 hours.

In some embodiments, the pharmaceutical composition is the form of an eye drop, a suspension, a gel, an ointment, an injectable solution, or a spray. In some embodiments, the pharmaceutical composition is the form of an eye drop. In some embodiments, the pharmaceutical composition is the form of a suspension. In some embodiments, the pharmaceutical composition is the form of a gel. In some embodiments, the pharmaceutical composition is the form of an ointment. In some embodiments, the pharmaceutical composition is the form of an injectable solution. In some embodiments, the pharmaceutical composition is the form of a spray.

In some embodiments, the pharmaceutical composition further comprises an effective amount of at least one additional therapeutic agent.

In some embodiments, the at least one additional therapeutic agent is chosen from anti-histamines. In some embodiments, the at least one additional therapeutic agent is chosen from pheniramine maleate, carbinoxamine maleate, S-(+)-chlorpheniramine maleate, diphenhydramine, hydroxyzine, and azelastine. In some embodiments, the at least one additional therapeutic agent is pheniramine maleate. In some embodiments, the at least one additional therapeutic agent is chosen from anti-histamines, anti-inflammatory agents, and antibiotics. In some embodiments, the at least one additional therapeutic agent is chosen from anti-inflammatory agents and antibiotics. In some embodiments, the at least one additional therapeutic agent is chosen from anti-inflammatory agents. In some embodiments, the at least one additional therapeutic agent is chosen from antibiotics.

In some embodiments, the at least one additional therapeutic agent is chosen from fluoroquinolones and $\alpha_2$-adrenergic agonists. In some embodiments, the at least one additional therapeutic agent is chosen from fluoroquinolones. In some embodiments, the at least one additional therapeutic agent is chosen from $\alpha_2$-adrenergic agonists.

In some embodiments, the at least one additional therapeutic agent is chosen from besifloxacin and brimonidine tartrate. In some embodiments, the at least one additional therapeutic agent is besifloxacin. In some embodiments, the at least one additional therapeutic agent is brimonidine tartrate.

In some embodiments, the effective amount of benzalkonium chloride is administered in the form of a pharmaceutical composition comprising 0.001% (w/v) to 0.02% (w/v) benzalkonium chloride. In some embodiments, the effective amount of benzalkonium chloride is administered in the form of a pharmaceutical composition comprising 0.004% (w/v) to 0.02% (w/v) benzalkonium chloride. In some embodiments, the effective amount of benzalkonium chloride is administered in the form of a pharmaceutical composition comprising 0.005% (w/v) to 0.02% (w/v) benzalkonium chloride.

In some embodiments, the effective amount of benzalkonium chloride is administered in the form of a pharmaceutical composition comprising 0.001% (w/v) to 0.01% (w/v) benzalkonium chloride. In some embodiments, the effective amount of benzalkonium chloride is administered in the form of a pharmaceutical composition comprising 0.004% (w/v) to 0.01% (w/v) benzalkonium chloride. In some embodiments, the effective amount of benzalkonium chloride is administered in the form of a pharmaceutical composition comprising 0.005% (w/v) to 0.01% (w/v) benzalkonium chloride.

In some embodiments, the effective amount of benzalkonium chloride is administered in the form of a pharmaceutical composition comprising 0.001% (w/v) benzalkonium chloride.

In some embodiments, the effective amount of benzalkonium chloride is administered in the form of a pharmaceutical composition comprising 0.0015% (w/v) benzalkonium chloride.

In some embodiments, the effective amount of benzalkonium chloride is administered in the form of a pharmaceutical composition comprising 0.002% (w/v) benzalkonium chloride.

In some embodiments, the effective amount of benzalkonium chloride is administered in the form of a pharmaceutical composition comprising 0.0025% (w/v) benzalkonium chloride.

In some embodiments, the effective amount of benzalkonium chloride is administered in the form of a pharmaceutical composition comprising 0.003% (w/v) benzalkonium chloride.

In some embodiments, the effective amount of benzalkonium chloride is administered in the form of a pharmaceutical composition comprising 0.0035% (w/v) benzalkonium chloride.

In some embodiments, the effective amount of benzalkonium chloride is administered in the form of a pharmaceutical composition comprising 0.004% (w/v) benzalkonium chloride.

In some embodiments, the effective amount of benzalkonium chloride is administered in the form of a pharmaceutical composition comprising 0.0045% (w/v) benzalkonium chloride.

In some embodiments, the effective amount of benzalkonium chloride is administered in the form of a pharmaceutical composition comprising 0.005% (w/v) benzalkonium chloride.

In some embodiments, the effective amount of benzalkonium chloride is administered in the form of a pharmaceutical composition comprising 0.0055% (w/v) benzalkonium chloride.

In some embodiments, the effective amount of benzalkonium chloride is administered in the form of a pharmaceutical composition comprising 0.006% (w/v) benzalkonium chloride.

In some embodiments, the effective amount of benzalkonium chloride is administered in the form of a pharmaceutical composition comprising 0.0065% (w/v) benzalkonium chloride.

In some embodiments, the effective amount of benzalkonium chloride is administered in the form of a pharmaceutical composition comprising 0.007% (w/v) benzalkonium chloride.

In some embodiments, the effective amount of benzalkonium chloride is administered in the form of a pharmaceutical composition comprising 0.0075% (w/v) benzalkonium chloride.

In some embodiments, the effective amount of benzalkonium chloride is administered in the form of a pharmaceutical composition comprising 0.008% (w/v) benzalkonium chloride.

In some embodiments, the effective amount of benzalkonium chloride is administered in the form of a pharmaceutical composition comprising 0.0085% (w/v) benzalkonium chloride.

In some embodiments, the effective amount of benzalkonium chloride is administered in the form of a pharmaceutical composition comprising 0.009% (w/v) benzalkonium chloride.

In some embodiments, the effective amount of benzalkonium chloride is administered in the form of a pharmaceutical composition comprising 0.0095% (w/v) benzalkonium chloride.

In some embodiments, the effective amount of benzalkonium chloride is administered in the form of a pharmaceutical composition comprising 0.01% (w/v) benzalkonium chloride.

In some embodiments, the effective amount of benzalkonium chloride is administered in the form of a pharmaceutical composition comprising 0.0125% (w/v) benzalkonium chloride.

In some embodiments, the effective amount of benzalkonium chloride is administered in the form of a pharmaceutical composition comprising 0.015% (w/v) benzalkonium chloride.

In some embodiments, the effective amount of benzalkonium chloride is administered in the form of a pharmaceutical composition comprising 0.0175% (w/v) benzalkonium chloride.

In some embodiments, the effective amount of benzalkonium chloride is administered in the form of a pharmaceutical composition comprising 0.02% (w/v) benzalkonium chloride.

In some embodiments, the pharmaceutical composition is chosen from Acular®, Advanced Eye Relief Dry Eye Lubricant Eye Drops, Alaway®, Alomide®, Alphagan®, AzaSite®, Azopt®, Bepreve™, Betagan®, Betoptic S®, Besivance®, Children's Alaway®, Ciloxan®, Cosopt®, Elestat®, FML®, Istalol®, Lastacaft®, Lotemax® gel (loteprednol 0.5%), Lotemax® SM gel (loteprednol 0.38%), Lotemax® suspension (loteprednol 0.5%), Lumify®, Lumigan®, Maxidex®, Naphcon-A®, Nevanac®, Ocuflox®, Opcon-A®, Optivar®, Pataday™, Patanol®, Polytrim®, Pred Forte®, Rescula®, Soothe Long Lasting Hydration, Timoptic®, Travatan®, Trusopt®, Xalatan®, Xibrom™, Zaditor®, Zerviate™ and Zymar®.

In some embodiments, the pharmaceutical composition is chosen from Advanced Eye Relief Dry Eye Lubricant Eye Drops, Alaway®, Children's Alaway®, Lumify®, Naphcon-A®, Opcon-A®, Soothe Long Lasting Hydration, and Zaditor®.

In some embodiments, the pharmaceutical composition is chosen from Alphagan®, Azopt®, Betagan®, Betoptic S®, Cosopt®, Istalol®, Lumigan®, Rescula®, Timoptic®, Travatan®, Trusopt®, and Xalatan®.

In some embodiments, the pharmaceutical composition is chosen from Alomide®, Bepreve™, Elestat®, Lastacaft®, Optivar®, Pataday™, Patanol®, and Zerviate™.

In some embodiments, the pharmaceutical composition is chosen from FML®, Lotemax® gel (loteprednol 0.5%), Lotemax® SM gel (loteprednol 0.38%), Lotemax® suspension (loteprednol 0.5%), Maxidex®, and Pred Forte®.

In some embodiments, the pharmaceutical composition is chosen from AzaSite®, Ciloxan®, Ocuflox®, Polytrim®, and Zymar®.

In some embodiments, the pharmaceutical composition is chosen from Acular®, Nevanac®, and Xibrom™.

In some embodiments, the pharmaceutical composition is chosen from Lumify®, Besivance®, and Opcon-A®. In some embodiments, the pharmaceutical composition is Lumify®. In some embodiments, the pharmaceutical composition is Besivance®. In some embodiments, the pharmaceutical composition is Opcon-A®.

In some embodiments, the effective amount of benzalkonium chloride is topically administered. In some embodiments, the effective amount of benzalkonium chloride is administered to at least one eye of a subject. In some embodiments, the effective amount of benzalkonium chloride is topically administered to at least one eye of a subject. In some embodiments, the effective amount of benzalkonium chloride is topically administered to one eye of a subject. In some embodiments, the effective amount of benzalkonium chloride is topically administered to both eyes of a subject.

In some embodiments, the methods comprise administering an effective amount of benzalkonium chloride in combination with an effective amount of at least one additional therapeutic agent. In some embodiments, the at least one additional therapeutic agent is chosen from anti-histamines. In some embodiments, the at least one additional therapeutic agent is chosen from pheniramine maleate, carbinoxamine maleate, S-(+)-chlorpheniramine maleate, diphenhydramine, hydroxyzine, and azelastine. In some embodiments, the at least one additional therapeutic agent is pheniramine maleate. In some embodiments, the at least one additional therapeutic agent is chosen from anti-histamines, anti-inflammatory agents, and antibiotics. In some embodiments, the at least one additional therapeutic agent is chosen from anti-inflammatory agents and antibiotics. In some embodiments, the at least one additional therapeutic agent is chosen from fluoroquinolones and $\alpha_2$-adrenergic agonists. In some embodiments, the at least one additional therapeutic agent is chosen from besifloxacin and brimonidine tartrate. In some embodiments, the at least one additional therapeutic agent is besifloxacin. In some embodiments, the at least one additional therapeutic agent is brimonidine tartrate.

In some embodiments, treating at least one ocular manifestation of COVID-19 comprises treating at least one disease or condition chosen from eye redness, conjunctivitis, keratoconjunctivitis, dry eye disease, blurred vision, conjunctival hyperaemia, ocular irritation, foreign body sensation, epiphora, eyelid edema, and chemosis.

In some embodiments, treating at least one ocular manifestation of COVID-19 comprises treating eye redness. In some embodiments, treating at least one ocular manifestation of COVID-19 comprises treating conjunctivitis. In some embodiments, treating at least one ocular manifestation of COVID-19 comprises treating keratoconjunctivitis. In some embodiments, treating at least one ocular manifestation of COVID-19 comprises treating dry eye disease. In some embodiments, treating at least one ocular manifestation of COVID-19 comprises treating blurred vision. In some embodiments, treating at least one ocular manifestation of COVID-19 comprises treating conjunctival hyperaemia. In some embodiments, treating at least one ocular manifestation of COVID-19 comprises treating ocular irritation. In some embodiments, treating at least one ocular manifestation of COVID-19 comprises treating foreign body sensation. In some embodiments, treating at least one ocular manifestation of COVID-19 comprises treating epiphora. In some embodiments, treating at least one ocular manifestation of COVID-19 comprises treating eyelid edema. In some embodiments, treating at least one ocular manifestation of COVID-19 treating comprises chemosis.

In some embodiments, treating at least one ocular manifestation of COVID-19 comprises improving visual acuity.

In some embodiments, treating at least one ocular manifestation of COVID-19 comprises reducing eye redness, ocular irritation, or foreign body sensation. In some embodiments, treating at least one ocular manifestation of COVID-19 comprises reducing eye redness. In some embodiments, treating at least one ocular manifestation of COVID-19 comprises reducing ocular irritation. In some embodiments, treating at least one ocular manifestation of COVID-19 comprises reducing foreign body sensation.

Some embodiments of this disclosure related to methods for reducing a risk of SARS-CoV-2 ocular transmission comprising administering to a subject in need thereof an effective amount of benzalkonium chloride.

In some embodiments, the effective amount of benzalkonium chloride is administered in the form of a pharmaceutical composition. In some embodiments, the effective amount of benzalkonium chloride is administered in the form of a pharmaceutical composition every 6 to 8 hours. In some embodiments, the effective amount of benzalkonium chloride is administered in the form of a pharmaceutical composition every 8 hours.

In some embodiments, the pharmaceutical composition is the form of an eye drop, a suspension, a gel, an ointment, an injectable solution, or a spray. In some embodiments, the pharmaceutical composition is the form of an eye drop. In some embodiments, the pharmaceutical composition is the form of a suspension. In some embodiments, the pharmaceutical composition is the form of a gel. In some embodiments, the pharmaceutical composition is the form of an ointment. In some embodiments, the pharmaceutical composition is the form of an injectable solution. In some embodiments, the pharmaceutical composition is the form of a spray.

In some embodiments, the pharmaceutical composition further comprises an effective amount of at least one additional therapeutic agent.

In some embodiments, the at least one additional therapeutic agent is chosen from anti-histamines. In some embodiments, the at least one additional therapeutic agent is chosen from pheniramine maleate, carbinoxamine maleate, S-(+)-chlorpheniramine maleate, diphenhydramine, hydroxyzine, and azelastine. In some embodiments, the at least one additional therapeutic agent is pheniramine maleate. In some embodiments, the at least one additional therapeutic agent is chosen from anti-histamines, anti-inflammatory agents, and antibiotics. In some embodiments, the at least one additional therapeutic agent is chosen from anti-inflammatory agents and antibiotics. In some embodiments, the at least one additional therapeutic agent is chosen from anti-inflammatory agents. In some embodiments, the at least one additional therapeutic agent is chosen from antibiotics.

In some embodiments, the at least one additional therapeutic agent is chosen from fluoroquinolones and $\alpha_2$-adrenergic agonists. In some embodiments, the at least one additional therapeutic agent is chosen from fluoroquinolones. In some embodiments, the at least one additional therapeutic agent is chosen from $\alpha_2$-adrenergic agonists.

In some embodiments, the at least one additional therapeutic agent is chosen from besifloxacin and brimonidine tartrate. In some embodiments, the at least one additional therapeutic agent is besifloxacin. In some embodiments, the at least one additional therapeutic agent is brimonidine tartrate.

In some embodiments, the effective amount of benzalkonium chloride is administered in the form of a pharmaceutical composition comprising 0.001% (w/v) to 0.02% (w/v) benzalkonium chloride. In some embodiments, the effective amount of benzalkonium chloride is administered in the form of a pharmaceutical composition comprising 0.004% (w/v) to 0.02% (w/v) benzalkonium chloride. In some embodiments, the effective amount of benzalkonium chloride is administered in the form of a pharmaceutical composition comprising 0.005% (w/v) to 0.02% (w/v) benzalkonium chloride.

In some embodiments, the effective amount of benzalkonium chloride is administered in the form of a pharmaceutical composition comprising 0.001% (w/v) to 0.01% (w/v) benzalkonium chloride. In some embodiments, the effective amount of benzalkonium chloride is administered in the form of a pharmaceutical composition comprising 0.004% (w/v) to 0.01% (w/v) benzalkonium chloride. In some embodiments, the effective amount of benzalkonium chloride is administered in the form of a pharmaceutical composition comprising 0.005% (w/v) to 0.01% (w/v) benzalkonium chloride.

In some embodiments, the effective amount of benzalkonium chloride is administered in the form of a pharmaceutical composition comprising 0.001% (w/v) benzalkonium chloride.

In some embodiments, the effective amount of benzalkonium chloride is administered in the form of a pharmaceutical composition comprising 0.0015% (w/v) benzalkonium chloride.

In some embodiments, the effective amount of benzalkonium chloride is administered in the form of a pharmaceutical composition comprising 0.002% (w/v) benzalkonium chloride.

In some embodiments, the effective amount of benzalkonium chloride is administered in the form of a pharmaceutical composition comprising 0.0025% (w/v) benzalkonium chloride.

In some embodiments, the effective amount of benzalkonium chloride is administered in the form of a pharmaceutical composition comprising 0.003% (w/v) benzalkonium chloride.

In some embodiments, the effective amount of benzalkonium chloride is administered in the form of a pharmaceutical composition comprising 0.0035% (w/v) benzalkonium chloride.

In some embodiments, the effective amount of benzalkonium chloride is administered in the form of a pharmaceutical composition comprising 0.004% (w/v) benzalkonium chloride.

In some embodiments, the effective amount of benzalkonium chloride is administered in the form of a pharmaceutical composition comprising 0.0045% (w/v) benzalkonium chloride.

In some embodiments, the effective amount of benzalkonium chloride is administered in the form of a pharmaceutical composition comprising 0.005% (w/v) benzalkonium chloride.

In some embodiments, the effective amount of benzalkonium chloride is administered in the form of a pharmaceutical composition comprising 0.0055% (w/v) benzalkonium chloride.

In some embodiments, the effective amount of benzalkonium chloride is administered in the form of a pharmaceutical composition comprising 0.006% (w/v) benzalkonium chloride.

In some embodiments, the effective amount of benzalkonium chloride is administered in the form of a pharmaceutical composition comprising 0.0065% (w/v) benzalkonium chloride.

In some embodiments, the effective amount of benzalkonium chloride is administered in the form of a pharmaceutical composition comprising 0.007% (w/v) benzalkonium chloride.

In some embodiments, the effective amount of benzalkonium chloride is administered in the form of a pharmaceutical composition comprising 0.0075% (w/v) benzalkonium chloride.

In some embodiments, the effective amount of benzalkonium chloride is administered in the form of a pharmaceutical composition comprising 0.008% (w/v) benzalkonium chloride.

In some embodiments, the effective amount of benzalkonium chloride is administered in the form of a pharmaceutical composition comprising 0.0085% (w/v) benzalkonium chloride.

In some embodiments, the effective amount of benzalkonium chloride is administered in the form of a pharmaceutical composition comprising 0.009% (w/v) benzalkonium chloride.

In some embodiments, the effective amount of benzalkonium chloride is administered in the form of a pharmaceutical composition comprising 0.0095% (w/v) benzalkonium chloride.

In some embodiments, the effective amount of benzalkonium chloride is administered in the form of a pharmaceutical composition comprising 0.01% (w/v) benzalkonium chloride.

In some embodiments, the effective amount of benzalkonium chloride is administered in the form of a pharmaceutical composition comprising 0.0125% (w/v) benzalkonium chloride.

In some embodiments, the effective amount of benzalkonium chloride is administered in the form of a pharmaceutical composition comprising 0.015% (w/v) benzalkonium chloride.

In some embodiments, the effective amount of benzalkonium chloride is administered in the form of a pharmaceutical composition comprising 0.0175% (w/v) benzalkonium chloride.

In some embodiments, the effective amount of benzalkonium chloride is administered in the form of a pharmaceutical composition comprising 0.02% (w/v) benzalkonium chloride.

In some embodiments, the pharmaceutical composition is chosen from Acular®, Advanced Eye Relief Dry Eye Lubricant Eye Drops, Alaway®, Alomide®, Alphagan®, AzaSite®, Azopt®, Bepreve™, Betagan®, Betoptic S®, Besivance®, Children's Alaway®, Ciloxan®, Cosopt®, Elestat®, FML®, Istalol®, Lastacaft®, Lotemax® gel (loteprednol 0.5%), Lotemax® SM gel (loteprednol 0.38%), Lotemax® suspension (loteprednol 0.5%), Lumify®, Lumigan®, Maxidex®, Naphcon-A®, Nevanac®, Ocuflox®, Opcon-A®, Optivar®, Pataday™, Patanol®, Polytrim®, Pred Forte®, Rescula®, Soothe Long Lasting Hydration, Timoptic®, Travatan®, Trusopt®, Xalatan®, Xibrom™, Zaditor®, Zerviate™ and Zymar®.

In some embodiments, the pharmaceutical composition is chosen from Advanced Eye Relief Dry Eye Lubricant Eye Drops, Alaway®, Children's Alaway®, Lumify®, Naphcon-A®, Opcon-A®, Soothe Long Lasting Hydration, and Zaditor®.

In some embodiments, the pharmaceutical composition is chosen from Alphagan®, Azopt®, Betagan®, Betoptic S®, Cosopt®, Istalol®, Lumigan®, Rescula®, Timoptic®, Travatan®, Trusopt®, and Xalatan®.

In some embodiments, the pharmaceutical composition is chosen from Alomide®, Bepreve™, Elestat®, Lastacaft®, Optivar®, Pataday™, Patanol®, and Zerviate™.

In some embodiments, the pharmaceutical composition is chosen from FML®, Lotemax® gel (loteprednol 0.5%), Lotemax® SM gel (loteprednol 0.38%), Lotemax® suspension (loteprednol 0.5%), Maxidex®, and Pred Forte®.

In some embodiments, the pharmaceutical composition is chosen from AzaSite®, Ciloxan®, Ocuflox®, Polytrim®, and Zymar®.

In some embodiments, the pharmaceutical composition is chosen from Acular®, Nevanac®, and Xibrom™.

In some embodiments, the pharmaceutical composition is chosen from Lumify®, Besivance®, and Opcon-A®. In some embodiments, the pharmaceutical composition is Lumify®. In some embodiments, the pharmaceutical composition is Besivance®. In some embodiments, the pharmaceutical composition is Opcon-A®.

In some embodiments, the effective amount of benzalkonium chloride is topically administered. In some embodiments, the effective amount of benzalkonium chloride is administered to at least one eye of a subject. In some embodiments, the effective amount of benzalkonium chloride is topically administered to at least one eye of a subject. In some embodiments, the effective amount of benzalkonium chloride is topically administered to one eye of a subject. In some embodiments, the effective amount of benzalkonium chloride is topically administered to both eyes of a subject.

In some embodiments, the methods comprise administering an effective amount of benzalkonium chloride in combination with an effective amount of at least one additional therapeutic agent. In some embodiments, the at least one additional therapeutic agent is chosen from anti-histamines. In some embodiments, the at least one additional therapeutic agent is chosen from pheniramine maleate, carbinoxamine maleate, S-(+)-chlorpheniramine maleate, diphenhydramine, hydroxyzine, and azelastine. In some embodiments, the at least one additional therapeutic agent is pheniramine maleate. In some embodiments, the at least one additional therapeutic agent is chosen from anti-histamines, anti-inflammatory agents, and antibiotics. In some embodiments, the at least one additional therapeutic agent is chosen from anti-inflammatory agents and antibiotics. In some embodiments, the at least one additional therapeutic agent is chosen from fluoroquinolones and $\alpha_2$-adrenergic agonists.

In some embodiments, the at least one additional therapeutic agent is chosen from besifloxacin and brimonidine tartrate. In some embodiments, the at least one additional therapeutic agent is besifloxacin. In some embodiments, the at least one additional therapeutic agent is brimonidine tartrate.

Some embodiments of this disclosure relate to methods for preventing coronavirus disease 2019 (COVID-19) comprising administering to a subject in need thereof an effective amount of benzalkonium chloride.

In some embodiments, the effective amount of benzalkonium chloride is administered in the form of a pharmaceutical composition. In some embodiments, the effective amount of benzalkonium chloride is administered in the form of a pharmaceutical composition every 6 to 8 hours. In some embodiments, the effective amount of benzalkonium chloride is administered in the form of a pharmaceutical composition every 8 hours.

In some embodiments, the pharmaceutical composition is the form of an eye drop, a suspension, a gel, an ointment, an injectable solution, or a spray. In some embodiments, the pharmaceutical composition is the form of an eye drop. In some embodiments, the pharmaceutical composition is the form of a suspension. In some embodiments, the pharmaceutical composition is the form of a gel. In some embodiments, the pharmaceutical composition is the form of an ointment. In some embodiments, the pharmaceutical composition is the form of an injectable solution. In some embodiments, the pharmaceutical composition is the form of a spray.

In some embodiments, the pharmaceutical composition further comprises an effective amount of at least one additional therapeutic agent.

In some embodiments, the at least one additional therapeutic agent is chosen from anti-histamines. In some embodiments, the at least one additional therapeutic agent is chosen from pheniramine maleate, carbinoxamine maleate, S-(+)-chlorpheniramine maleate, diphenhydramine, hydroxyzine, and azelastine. In some embodiments, the at least one additional therapeutic agent is pheniramine maleate. In some embodiments, the at least one additional therapeutic agent is chosen from anti-histamines, anti-inflammatory agents, and antibiotics. In some embodiments, the at least one additional therapeutic agent is chosen from anti-inflammatory agents and antibiotics. In some embodiments, the at least one additional therapeutic agent is chosen from anti-inflammatory agents. In some embodiments, the at least one additional therapeutic agent is chosen from antibiotics.

In some embodiments, the at least one additional therapeutic agent is chosen from fluoroquinolones and $\alpha_2$-adrenergic agonists. In some embodiments, the at least one additional therapeutic agent is chosen from fluoroquinolones. In some embodiments, the at least one additional therapeutic agent is chosen from $\alpha_2$-adrenergic agonists.

In some embodiments, the at least one additional therapeutic agent is chosen from besifloxacin and brimonidine tartrate. In some embodiments, the at least one additional therapeutic agent is besifloxacin. In some embodiments, the at least one additional therapeutic agent is brimonidine tartrate.

In some embodiments, the effective amount of benzalkonium chloride is administered in the form of a pharmaceutical composition comprising 0.001% (w/v) to 0.02% (w/v) benzalkonium chloride. In some embodiments, the effective amount of benzalkonium chloride is administered in the form of a pharmaceutical composition comprising 0.004% (w/v) to 0.02% (w/v) benzalkonium chloride. In some embodiments, the effective amount of benzalkonium chloride is administered in the form of a pharmaceutical composition comprising 0.005% (w/v) to 0.02% (w/v) benzalkonium chloride.

In some embodiments, the effective amount of benzalkonium chloride is administered in the form of a pharmaceutical composition comprising 0.001% (w/v) to 0.01% (w/v) benzalkonium chloride. In some embodiments, the effective amount of benzalkonium chloride is administered in the form of a pharmaceutical composition comprising 0.004% (w/v) to 0.01% (w/v) benzalkonium chloride. In some embodiments, the effective amount of benzalkonium chloride is administered in the form of a pharmaceutical composition comprising 0.005% (w/v) to 0.01% (w/v) benzalkonium chloride.

In some embodiments, the effective amount of benzalkonium chloride is administered in the form of a pharmaceutical composition comprising 0.001% (w/v) benzalkonium chloride.

In some embodiments, the effective amount of benzalkonium chloride is administered in the form of a pharmaceutical composition comprising 0.0015% (w/v) benzalkonium chloride.

In some embodiments, the effective amount of benzalkonium chloride is administered in the form of a pharmaceutical composition comprising 0.002% (w/v) benzalkonium chloride.

In some embodiments, the effective amount of benzalkonium chloride is administered in the form of a pharmaceutical composition comprising 0.0025% (w/v) benzalkonium chloride.

In some embodiments, the effective amount of benzalkonium chloride is administered in the form of a pharmaceutical composition comprising 0.003% (w/v) benzalkonium chloride.

In some embodiments, the effective amount of benzalkonium chloride is administered in the form of a pharmaceutical composition comprising 0.0035% (w/v) benzalkonium chloride.

In some embodiments, the effective amount of benzalkonium chloride is administered in the form of a pharmaceutical composition comprising 0.004% (w/v) benzalkonium chloride.

In some embodiments, the effective amount of benzalkonium chloride is administered in the form of a pharmaceutical composition comprising 0.0045% (w/v) benzalkonium chloride.

In some embodiments, the effective amount of benzalkonium chloride is administered in the form of a pharmaceutical composition comprising 0.005% (w/v) benzalkonium chloride.

In some embodiments, the effective amount of benzalkonium chloride is administered in the form of a pharmaceutical composition comprising 0.0055% (w/v) benzalkonium chloride.

In some embodiments, the effective amount of benzalkonium chloride is administered in the form of a pharmaceutical composition comprising 0.006% (w/v) benzalkonium chloride.

In some embodiments, the effective amount of benzalkonium chloride is administered in the form of a pharmaceutical composition comprising 0.0065% (w/v) benzalkonium chloride.

In some embodiments, the effective amount of benzalkonium chloride is administered in the form of a pharmaceutical composition comprising 0.007% (w/v) benzalkonium chloride.

In some embodiments, the effective amount of benzalkonium chloride is administered in the form of a pharmaceutical composition comprising 0.0075% (w/v) benzalkonium chloride.

In some embodiments, the effective amount of benzalkonium chloride is administered in the form of a pharmaceutical composition comprising 0.008% (w/v) benzalkonium chloride.

In some embodiments, the effective amount of benzalkonium chloride is administered in the form of a pharmaceutical composition comprising 0.0085% (w/v) benzalkonium chloride.

In some embodiments, the effective amount of benzalkonium chloride is administered in the form of a pharmaceutical composition comprising 0.009% (w/v) benzalkonium chloride.

In some embodiments, the effective amount of benzalkonium chloride is administered in the form of a pharmaceutical composition comprising 0.0095% (w/v) benzalkonium chloride.

In some embodiments, the effective amount of benzalkonium chloride is administered in the form of a pharmaceutical composition comprising 0.01% (w/v) benzalkonium chloride.

In some embodiments, the effective amount of benzalkonium chloride is administered in the form of a pharmaceutical composition comprising 0.0125% (w/v) benzalkonium chloride.

In some embodiments, the effective amount of benzalkonium chloride is administered in the form of a pharmaceutical composition comprising 0.015% (w/v) benzalkonium chloride.

In some embodiments, the effective amount of benzalkonium chloride is administered in the form of a pharmaceutical composition comprising 0.0175% (w/v) benzalkonium chloride.

In some embodiments, the effective amount of benzalkonium chloride is administered in the form of a pharmaceutical composition comprising 0.02% (w/v) benzalkonium chloride.

In some embodiments, the pharmaceutical composition is chosen from Acular®, Advanced Eye Relief Dry Eye Lubricant Eye Drops, Alaway®, Alomide®, Alphagan®, AzaSite®, Azopt®, Bepreve™, Betagan®, Betoptic S®, Besivance®, Children's Alaway®, Ciloxan®, Cosopt®, Elestat®, FML®, Istalol®, Lastacaft®, Lotemax® gel (loteprednol 0.5%), Lotemax® SM gel (loteprednol 0.38%), Lotemax® suspension (loteprednol 0.5%), Lumify®, Lumigan®, Maxidex®, Naphcon-A®, Nevanac®, Ocuflox®, Opcon-A®, Optivar®, Pataday™, Patanol®, Polytrim®, Pred Forte®, Rescula®, Soothe Long Lasting Hydration, Timoptic®, Travatan®, Trusopt®, Xalatan®, Xibrom™, Zaditor®, Zerviate™ and Zymar®.

In some embodiments, the pharmaceutical composition is chosen from Advanced Eye Relief Dry Eye Lubricant Eye Drops, Alaway®, Children's Alaway®, Lumify®, Naphcon-A®, Opcon-A®, Soothe Long Lasting Hydration, and Zaditor®.

In some embodiments, the pharmaceutical composition is chosen from Alphagan®, Azopt®, Betagan®, Betoptic S®, Cosopt®, Istalol®, Lumigan®, Rescula®, Timoptic®, Travatan®, Trusopt®, and Xalatan®.

In some embodiments, the pharmaceutical composition is chosen from Alomide®, Bepreve™, Elestat®, Lastacaft®, Optivar®, Pataday™, Patanol®, and Zerviate™.

In some embodiments, the pharmaceutical composition is chosen from FML®, Lotemax® gel (loteprednol 0.5%), Lotemax® SM gel (loteprednol 0.38%), Lotemax® suspension (loteprednol 0.5%), Maxidex®, and Pred Forte®.

In some embodiments, the pharmaceutical composition is chosen from AzaSite®, Ciloxan®, Ocuflox®, Polytrim®, and Zymar®.

In some embodiments, the pharmaceutical composition is chosen from Acular®, Nevanac®, and Xibrom™.

In some embodiments, the pharmaceutical composition is chosen from Lumify®, Besivance®, and Opcon-A®. In some embodiments, the pharmaceutical composition is Lumify®. In some embodiments, the pharmaceutical composition is Besivance®. In some embodiments, the pharmaceutical composition is Opcon-A®.

In some embodiments, the effective amount of benzalkonium chloride is topically administered. In some embodiments, the effective amount of benzalkonium chloride is administered to at least one eye of a subject. In some embodiments, the effective amount of benzalkonium chloride is topically administered to at least one eye of a subject. In some embodiments, the effective amount of benzalkonium chloride is topically administered to one eye of a subject. In some embodiments, the effective amount of benzalkonium chloride is topically administered to both eyes of a subject.

In some embodiments, the methods comprise administering an effective amount of benzalkonium chloride in combination with an effective amount of at least one additional therapeutic agent. In some embodiments, the at least one additional therapeutic agent is chosen from anti-histamines. In some embodiments, the at least one additional therapeutic agent is chosen from pheniramine maleate, carbinoxamine maleate, S-(+)-chlorpheniramine maleate, diphenhydramine, hydroxyzine, and azelastine. In some embodiments, the at least one additional therapeutic agent is pheniramine maleate. In some embodiments, the at least one additional therapeutic agent is chosen from anti-histamines, anti-inflammatory agents, and antibiotics. In some embodiments, the at least one additional therapeutic agent is chosen from anti-inflammatory agents and antibiotics. In some embodiments, the at least one additional therapeutic agent is chosen from fluoroquinolones and $\alpha_2$-adrenergic agonists.

In some embodiments, the at least one additional therapeutic agent is chosen from besifloxacin and brimonidine tartrate. In some embodiments, the at least one additional therapeutic agent is besifloxacin. In some embodiments, the at least one additional therapeutic agent is brimonidine tartrate.

In some embodiments, preventing COVID-19 comprises preventing at least one ocular manifestation of COVID-19. In some embodiments, preventing COVID-19 comprises preventing at least one ocular manifestation of COVID-19 chosen from eye redness, conjunctivitis, keratoconjunctivitis, dry eye disease, blurred vision, conjunctival hyperaemia, ocular irritation, foreign body sensation, epiphora, eyelid edema, and chemosis.

Some embodiments of this disclosure relate to methods for reducing an ocular SARS-CoV-2 viral load comprising administering to a subject in need thereof an effective amount of benzalkonium chloride.

In some embodiments, the effective amount of benzalkonium chloride is administered in the form of a pharmaceutical composition. In some embodiments, the effective amount of benzalkonium chloride is administered in the form of a pharmaceutical composition every 6 to 8 hours. In some embodiments, the effective amount of benzalkonium chloride is administered in the form of a pharmaceutical composition every 8 hours.

In some embodiments, the pharmaceutical composition is the form of an eye drop, a suspension, a gel, an ointment, an injectable solution, or a spray. In some embodiments, the pharmaceutical composition is the form of an eye drop. In some embodiments, the pharmaceutical composition is the form of a suspension. In some embodiments, the pharmaceutical composition is the form of a gel. In some embodiments, the pharmaceutical composition is the form of an ointment. In some embodiments, the pharmaceutical composition is the form of an injectable solution. In some embodiments, the pharmaceutical composition is the form of a spray.

In some embodiments, the pharmaceutical composition further comprises an effective amount of at least one additional therapeutic agent.

In some embodiments, the at least one additional therapeutic agent is chosen from anti-histamines. In some embodiments, the at least one additional therapeutic agent is chosen from pheniramine maleate, carbinoxamine maleate, S-(+)-chlorpheniramine maleate, diphenhydramine, hydroxyzine, and azelastine. In some embodiments, the at least one additional therapeutic agent is pheniramine maleate. In some embodiments, the at least one additional therapeutic agent is chosen from anti-histamines, anti-inflammatory agents, and antibiotics. In some embodiments, the at least one additional therapeutic agent is chosen from anti-inflammatory agents and antibiotics. In some embodiments, the at least one additional therapeutic agent is chosen from anti-inflammatory agents. In some embodiments, the at least one additional therapeutic agent is chosen from antibiotics.

In some embodiments, the at least one additional therapeutic agent is chosen from fluoroquinolones and $\alpha_2$-adrenergic agonists. In some embodiments, the at least one additional therapeutic agent is chosen from fluoroquinolones. In some embodiments, the at least one additional therapeutic agent is chosen from $\alpha_2$-adrenergic agonists.

In some embodiments, the at least one additional therapeutic agent is chosen from besifloxacin and brimonidine tartrate. In some embodiments, the at least one additional therapeutic agent is besifloxacin. In some embodiments, the at least one additional therapeutic agent is brimonidine tartrate.

In some embodiments, the effective amount of benzalkonium chloride is administered in the form of a pharmaceutical composition comprising 0.001% (w/v) to 0.02% (w/v) benzalkonium chloride. In some embodiments, the effective amount of benzalkonium chloride is administered in the form of a pharmaceutical composition comprising 0.004% (w/v) to 0.02% (w/v) benzalkonium chloride. In some embodiments, the effective amount of benzalkonium chloride is administered in the form of a pharmaceutical composition comprising 0.005% (w/v) to 0.02% (w/v) benzalkonium chloride.

In some embodiments, the effective amount of benzalkonium chloride is administered in the form of a pharmaceutical composition comprising 0.001% (w/v) to 0.01% (w/v) benzalkonium chloride. In some embodiments, the effective amount of benzalkonium chloride is administered in the form of a pharmaceutical composition comprising 0.004% (w/v) to 0.01% (w/v) benzalkonium chloride. In some embodiments, the effective amount of benzalkonium chloride is administered in the form of a pharmaceutical composition comprising 0.005% (w/v) to 0.01% (w/v) benzalkonium chloride.

In some embodiments, the effective amount of benzalkonium chloride is administered in the form of a pharmaceutical composition comprising 0.001% (w/v) benzalkonium chloride.

In some embodiments, the effective amount of benzalkonium chloride is administered in the form of a pharmaceutical composition comprising 0.0015% (w/v) benzalkonium chloride.

In some embodiments, the effective amount of benzalkonium chloride is administered in the form of a pharmaceutical composition comprising 0.002% (w/v) benzalkonium chloride.

In some embodiments, the effective amount of benzalkonium chloride is administered in the form of a pharmaceutical composition comprising 0.0025% (w/v) benzalkonium chloride.

In some embodiments, the effective amount of benzalkonium chloride is administered in the form of a pharmaceutical composition comprising 0.003% (w/v) benzalkonium chloride.

In some embodiments, the effective amount of benzalkonium chloride is administered in the form of a pharmaceutical composition comprising 0.0035% (w/v) benzalkonium chloride.

In some embodiments, the effective amount of benzalkonium chloride is administered in the form of a pharmaceutical composition comprising 0.004% (w/v) benzalkonium chloride.

In some embodiments, the effective amount of benzalkonium chloride is administered in the form of a pharmaceutical composition comprising 0.0045% (w/v) benzalkonium chloride.

In some embodiments, the effective amount of benzalkonium chloride is administered in the form of a pharmaceutical composition comprising 0.005% (w/v) benzalkonium chloride.

In some embodiments, the effective amount of benzalkonium chloride is administered in the form of a pharmaceutical composition comprising 0.0055% (w/v) benzalkonium chloride.

In some embodiments, the effective amount of benzalkonium chloride is administered in the form of a pharmaceutical composition comprising 0.006% (w/v) benzalkonium chloride.

In some embodiments, the effective amount of benzalkonium chloride is administered in the form of a pharmaceutical composition comprising 0.0065% (w/v) benzalkonium chloride.

In some embodiments, the effective amount of benzalkonium chloride is administered in the form of a pharmaceutical composition comprising 0.007% (w/v) benzalkonium chloride.

In some embodiments, the effective amount of benzalkonium chloride is administered in the form of a pharmaceutical composition comprising 0.0075% (w/v) benzalkonium chloride.

In some embodiments, the effective amount of benzalkonium chloride is administered in the form of a pharmaceutical composition comprising 0.008% (w/v) benzalkonium chloride.

In some embodiments, the effective amount of benzalkonium chloride is administered in the form of a pharmaceutical composition comprising 0.0085% (w/v) benzalkonium chloride.

In some embodiments, the effective amount of benzalkonium chloride is administered in the form of a pharmaceutical composition comprising 0.009% (w/v) benzalkonium chloride.

In some embodiments, the effective amount of benzalkonium chloride is administered in the form of a pharmaceutical composition comprising 0.0095% (w/v) benzalkonium chloride.

In some embodiments, the effective amount of benzalkonium chloride is administered in the form of a pharmaceutical composition comprising 0.01% (w/v) benzalkonium chloride.

In some embodiments, the effective amount of benzalkonium chloride is administered in the form of a pharmaceutical composition comprising 0.0125% (w/v) benzalkonium chloride.

In some embodiments, the effective amount of benzalkonium chloride is administered in the form of a pharmaceutical composition comprising 0.015% (w/v) benzalkonium chloride.

In some embodiments, the effective amount of benzalkonium chloride is administered in the form of a pharmaceutical composition comprising 0.0175% (w/v) benzalkonium chloride.

In some embodiments, the effective amount of benzalkonium chloride is administered in the form of a pharmaceutical composition comprising 0.02% (w/v) benzalkonium chloride.

In some embodiments, the pharmaceutical composition is chosen from Acular®, Advanced Eye Relief Dry Eye Lubricant Eye Drops, Alaway®, Alomide®, Alphagan®, AzaSite®, Azopt®, Bepreve™, Betagan®, Betoptic S®, Besivance®, Children's Alaway®, Ciloxan®, Cosopt®, Elestat®, FML®, Istalol®, Lastacaft®, Lotemax® gel (loteprednol 0.5%), Lotemax® SM gel (loteprednol 0.38%), Lotemax® suspension (loteprednol 0.5%), Lumify®, Lumigan®, Maxidex®, Naphcon-A®, Nevanac®, Ocuflox®, Opcon-A®, Optivar®, Pataday™, Patanol®, Polytrim®, Pred Forte®, Rescula®, Soothe Long Lasting Hydration, Timoptic®, Travatan®, Trusopt®, Xalatan®, Xibrom™, Zaditor®, Zerviate™ and Zymar®.

In some embodiments, the pharmaceutical composition is chosen from Advanced Eye Relief Dry Eye Lubricant Eye Drops, Alaway®, Children's Alaway®, Lumify®, Naphcon-A®, Opcon-A®, Soothe Long Lasting Hydration, and Zaditor®.

In some embodiments, the pharmaceutical composition is chosen from Alphagan®, Azopt®, Betagan®, Betoptic S®, Cosopt®, Istalol®, Lumigan®, Rescula®, Timoptic®, Travatan®, Trusopt®, and Xalatan®.

In some embodiments, the pharmaceutical composition is chosen from Alomide®, Bepreve™, Elestat®, Lastacaft®, Optivar®, Pataday™, Patanol®, and Zerviate™.

In some embodiments, the pharmaceutical composition is chosen from FML®, Lotemax® gel (loteprednol 0.5%), Lotemax® SM gel (loteprednol 0.38%), Lotemax® suspension (loteprednol 0.5%), Maxidex®, and Pred Forte®.

In some embodiments, the pharmaceutical composition is chosen from AzaSite®, Ciloxan®, Ocuflox®, Polytrim®, and Zymar®.

In some embodiments, the pharmaceutical composition is chosen from Acular®, Nevanac®, and Xibrom™.

In some embodiments, the pharmaceutical composition is chosen from Lumify®, Besivance®, and Opcon-A®. In some embodiments, the pharmaceutical composition is Lumify®. In some embodiments, the pharmaceutical composition is Besivance®. In some embodiments, the pharmaceutical composition is Opcon-A®.

In some embodiments, the effective amount of benzalkonium chloride is topically administered. In some embodiments, the effective amount of benzalkonium chloride is administered to at least one eye of a subject. In some embodiments, the effective amount of benzalkonium chloride is topically administered to at least one eye of a subject. In some embodiments, the effective amount of benzalkonium chloride is topically administered to one eye of a subject. In some embodiments, the effective amount of benzalkonium chloride is topically administered to both eyes of a subject.

In some embodiments, the methods comprise administering an effective amount of benzalkonium chloride in combination with an effective amount of at least one additional therapeutic agent. In some embodiments, the at least one additional therapeutic agent is chosen from anti-histamines. In some embodiments, the at least one additional therapeutic agent is chosen from pheniramine maleate, carbinoxamine maleate, S-(+)-chlorpheniramine maleate, diphenhydramine, hydroxyzine, and azelastine. In some embodiments, the at least one additional therapeutic agent is pheniramine maleate. In some embodiments, the at least one additional therapeutic agent is chosen from anti-histamines, anti-inflammatory agents, and antibiotics. In some embodiments, the at least one additional therapeutic agent is chosen from anti-inflammatory agents and antibiotics. In some embodiments, the at least one additional therapeutic agent is chosen from fluoroquinolones and $\alpha_2$-adrenergic agonists.

In some embodiments, the at least one additional therapeutic agent is chosen from besifloxacin and brimonidine tartrate. In some embodiments, the at least one additional therapeutic agent is besifloxacin. In some embodiments, the at least one additional therapeutic agent is brimonidine tartrate.

In some embodiments, reducing an ocular SARS-CoV-2 viral load comprises reducing the ocular SARS-CoV-2 viral load by 25% compared to a pre-treatment ocular SARS-CoV-2 viral load. In some embodiments, reducing an ocular SARS-CoV-2 viral load comprises reducing the ocular SARS-CoV-2 viral load by 50% compared to a pre-treatment ocular SARS-CoV-2 viral load. In some embodiments, reducing an ocular SARS-CoV-2 viral load comprises reducing the ocular SARS-CoV-2 viral load by 75% compared to a pre-treatment ocular SARS-CoV-2 viral load. In some embodiments, reducing an ocular SARS-CoV-2 viral load comprises reducing the ocular SARS-CoV-2 viral load by 80% compared to a pre-treatment ocular SARS-CoV-2 viral load. In some embodiments, reducing an ocular SARS-CoV-2 viral load comprises reducing the ocular SARS-CoV-2 viral load by 90% compared to a pre-treatment ocular SARS-CoV-2 viral load. In some embodiments, reducing an ocular SARS-CoV-2 viral load comprises reducing the ocular SARS-CoV-2 viral load by 95% compared to a pre-treatment ocular SARS-CoV-2 viral load.

Some embodiments of the present disclosure relate to methods for treating conjunctivitis comprising administering to a subject in need thereof an effective amount of benzalkonium chloride.

In some embodiments, treating conjunctivitis comprises treating viral conjunctivitis. In some embodiments, treating conjunctivitis comprises treating conjunctivitis of unknown etiology.

In some embodiments, the effective amount of benzalkonium chloride is administered in the form of a pharmaceutical composition.

In some embodiments, the effective amount of benzalkonium chloride is administered in the form of a pharmaceutical composition every 6 to 8 hours. In some embodiments, the effective amount of benzalkonium chloride is administered in the form of a pharmaceutical composition every 8 hours.

In some embodiments, the pharmaceutical composition is the form of an eye drop, a suspension, a gel, an ointment, an injectable solution, or a spray. In some embodiments, the pharmaceutical composition is the form of an eye drop. In some embodiments, the pharmaceutical composition is the form of a suspension. In some embodiments, the pharmaceutical composition is the form of a gel. In some embodiments, the pharmaceutical composition is the form of an ointment. In some embodiments, the pharmaceutical composition is the form of an injectable solution. In some embodiments, the pharmaceutical composition is the form of a spray.

In some embodiments, the pharmaceutical composition further comprises an effective amount of at least one additional therapeutic agent.

In some embodiments, the at least one additional therapeutic agent is chosen from anti-histamines. In some embodiments, the at least one additional therapeutic agent is chosen from pheniramine maleate, carbinoxamine maleate, S-(+)-chlorpheniramine maleate, diphenhydramine, hydroxyzine, and azelastine. In some embodiments, the at least one additional therapeutic agent is pheniramine maleate. In some embodiments, the at least one additional therapeutic agent is chosen from anti-histamines, anti-inflammatory agents, and antibiotics. In some embodiments, the at least one additional therapeutic agent is chosen from anti-inflammatory agents and antibiotics. In some embodiments, the at least one additional therapeutic agent is chosen from anti-inflammatory agents. In some embodiments, the at least one additional therapeutic agent is chosen from antibiotics.

In some embodiments, the at least one additional therapeutic agent is chosen from fluoroquinolones and $\alpha_2$-adrenergic agonists. In some embodiments, the at least one additional therapeutic agent is chosen from fluoroquinolones. In some embodiments, the at least one additional therapeutic agent is chosen from $\alpha_2$-adrenergic agonists.

In some embodiments, the at least one additional therapeutic agent is chosen from besifloxacin and brimonidine tartrate. In some embodiments, the at least one additional therapeutic agent is besifloxacin. In some embodiments, the at least one additional therapeutic agent is brimonidine tartrate.

In some embodiments, the effective amount of benzalkonium chloride is administered in the form of a pharmaceutical composition comprising 0.001% (w/v) to 0.02% (w/v) benzalkonium chloride. In some embodiments, the effective amount of benzalkonium chloride is administered in the form of a pharmaceutical composition comprising 0.004% (w/v) to 0.02% (w/v) benzalkonium chloride. In some embodiments, the effective amount of benzalkonium chloride is administered in the form of a pharmaceutical composition comprising 0.005% (w/v) to 0.02% (w/v) benzalkonium chloride.

In some embodiments, the effective amount of benzalkonium chloride is administered in the form of a pharmaceutical composition comprising 0.001% (w/v) to 0.01% (w/v) benzalkonium chloride. In some embodiments, the effective amount of benzalkonium chloride is administered in the form of a pharmaceutical composition comprising 0.004% (w/v) to 0.01% (w/v) benzalkonium chloride. In some embodiments, the effective amount of benzalkonium chloride is administered in the form of a pharmaceutical composition comprising 0.005% (w/v) to 0.01% (w/v) benzalkonium chloride.

In some embodiments, the effective amount of benzalkonium chloride is administered in the form of a pharmaceutical composition comprising 0.001% (w/v) benzalkonium chloride.

In some embodiments, the effective amount of benzalkonium chloride is administered in the form of a pharmaceutical composition comprising 0.0015% (w/v) benzalkonium chloride.

In some embodiments, the effective amount of benzalkonium chloride is administered in the form of a pharmaceutical composition comprising 0.002% (w/v) benzalkonium chloride.

In some embodiments, the effective amount of benzalkonium chloride is administered in the form of a pharmaceutical composition comprising 0.0025% (w/v) benzalkonium chloride.

In some embodiments, the effective amount of benzalkonium chloride is administered in the form of a pharmaceutical composition comprising 0.003% (w/v) benzalkonium chloride.

In some embodiments, the effective amount of benzalkonium chloride is administered in the form of a pharmaceutical composition comprising 0.0035% (w/v) benzalkonium chloride.

In some embodiments, the effective amount of benzalkonium chloride is administered in the form of a pharmaceutical composition comprising 0.004% (w/v) benzalkonium chloride.

In some embodiments, the effective amount of benzalkonium chloride is administered in the form of a pharmaceutical composition comprising 0.0045% (w/v) benzalkonium chloride.

In some embodiments, the effective amount of benzalkonium chloride is administered in the form of a pharmaceutical composition comprising 0.005% (w/v) benzalkonium chloride.

In some embodiments, the effective amount of benzalkonium chloride is administered in the form of a pharmaceutical composition comprising 0.0055% (w/v) benzalkonium chloride.

In some embodiments, the effective amount of benzalkonium chloride is administered in the form of a pharmaceutical composition comprising 0.006% (w/v) benzalkonium chloride.

In some embodiments, the effective amount of benzalkonium chloride is administered in the form of a pharmaceutical composition comprising 0.0065% (w/v) benzalkonium chloride.

In some embodiments, the effective amount of benzalkonium chloride is administered in the form of a pharmaceutical composition comprising 0.007% (w/v) benzalkonium chloride.

In some embodiments, the effective amount of benzalkonium chloride is administered in the form of a pharmaceutical composition comprising 0.0075% (w/v) benzalkonium chloride.

In some embodiments, the effective amount of benzalkonium chloride is administered in the form of a pharmaceutical composition comprising 0.008% (w/v) benzalkonium chloride.

In some embodiments, the effective amount of benzalkonium chloride is administered in the form of a pharmaceutical composition comprising 0.0085% (w/v) benzalkonium chloride.

In some embodiments, the effective amount of benzalkonium chloride is administered in the form of a pharmaceutical composition comprising 0.009% (w/v) benzalkonium chloride.

In some embodiments, the effective amount of benzalkonium chloride is administered in the form of a pharmaceutical composition comprising 0.0095% (w/v) benzalkonium chloride.

In some embodiments, the effective amount of benzalkonium chloride is administered in the form of a pharmaceutical composition comprising 0.01% (w/v) benzalkonium chloride.

In some embodiments, the effective amount of benzalkonium chloride is administered in the form of a pharmaceutical composition comprising 0.0125% (w/v) benzalkonium chloride.

In some embodiments, the effective amount of benzalkonium chloride is administered in the form of a pharmaceutical composition comprising 0.015% (w/v) benzalkonium chloride.

In some embodiments, the effective amount of benzalkonium chloride is administered in the form of a pharmaceutical composition comprising 0.0175% (w/v) benzalkonium chloride.

In some embodiments, the effective amount of benzalkonium chloride is administered in the form of a pharmaceutical composition comprising 0.02% (w/v) benzalkonium chloride.

In some embodiments, the pharmaceutical composition is chosen from Acular®, Advanced Eye Relief Dry Eye Lubricant Eye Drops, Alaway®, Alomide®, Alphagan®, AzaSite®, Azopt®, Bepreve™, Betagan®, Betoptic S®, Besivance®, Children's Alaway®, Ciloxan®, Cosopt®, Elestat®, FML®, Istalol®, Lastacaft®, Lotemax® gel (loteprednol Lotemax® SM gel (loteprednol 0.38%), Lotemax® suspension (loteprednol 0.5%), Lumify®, Lumigan®, Maxidex®, Naphcon-A®, Nevanac®, Ocuflox®, Opcon-A®, Optivar®, Pataday™, Patanol®, Polytrim®, Pred Forte®, Rescula®, Soothe Long Lasting Hydration, Timoptic®, Travatan®, Trusopt®, Xalatan®, Xibrom™, Zaditor®, Zerviate™ and Zymar®.

In some embodiments, the pharmaceutical composition is chosen from Advanced Eye Relief Dry Eye Lubricant Eye Drops, Alaway®, Children's Alaway®, Lumify®, Naphcon-A®, Opcon-A®, Soothe Long Lasting Hydration, and Zaditor®.

In some embodiments, the pharmaceutical composition is chosen from Alphagan®, Azopt®, Betagan®, Betoptic S®, Cosopt®, Istalol®, Lumigan®, Rescula®, Timoptic®, Travatan®, Trusopt®, and Xalatan®.

In some embodiments, the pharmaceutical composition is chosen from Alomide®, Bepreve™, Elestat®, Lastacaft®, Optivar®, Pataday™, Patanol®, and Zerviate™.

In some embodiments, the pharmaceutical composition is chosen from FML®, Lotemax® gel (loteprednol 0.5%), Lotemax® SM gel (loteprednol 0.38%), Lotemax® suspension (loteprednol 0.5%), Maxidex®, and Pred Forte®.

In some embodiments, the pharmaceutical composition is chosen from AzaSite®, Ciloxan®, Ocuflox®, Polytrim®, and Zymar®.

In some embodiments, the pharmaceutical composition is chosen from Acular®, Nevanac®, and Xibrom™.

In some embodiments, the pharmaceutical composition is chosen from Lumify®, Besivance®, and Opcon-A®. In some embodiments, the pharmaceutical composition is Lumify®. In some embodiments, the pharmaceutical composition is Besivance®. In some embodiments, the pharmaceutical composition is Opcon-A®.

In some embodiments, the effective amount of benzalkonium chloride is topically administered. In some embodiments, the effective amount of benzalkonium chloride is administered to at least one eye of a subject. In some embodiments, the effective amount of benzalkonium chloride is topically administered to at least one eye of a subject. In some embodiments, the effective amount of benzalkonium chloride is topically administered to one eye of a subject. In some embodiments, the effective amount of benzalkonium chloride is topically administered to both eyes of a subject.

In some embodiments, the methods comprise administering an effective amount of benzalkonium chloride in combination with an effective amount of at least one additional therapeutic agent. In some embodiments, the at least one additional therapeutic agent is chosen from anti-histamines. In some embodiments, the at least one additional therapeutic agent is chosen from pheniramine maleate, carbinoxamine maleate, S-(+)-chlorpheniramine maleate, diphenhydramine, hydroxyzine, and azelastine. In some embodiments, the at least one additional therapeutic agent is pheniramine maleate. In some embodiments, the at least one additional therapeutic agent is chosen from anti-histamines, anti-inflammatory agents, and antibiotics. In some embodiments, the at least one additional therapeutic agent is chosen from anti-inflammatory agents and antibiotics. In some embodiments, the at least one additional therapeutic agent is chosen from fluoroquinolones and $\alpha_2$-adrenergic agonists.

In some embodiments, the at least one additional therapeutic agent is chosen from besifloxacin and brimonidine tartrate. In some embodiments, the at least one additional therapeutic agent is besifloxacin. In some embodiments, the at least one additional therapeutic agent is brimonidine tartrate.

Some embodiments of the present disclosure relate to methods for preventing conjunctivitis comprising administering to a subject in need thereof an effective amount of benzalkonium chloride.

In some embodiments, the subject exhibits at least one symptom of a viral infection. In some embodiments, the subject exhibits at least one symptom of a SARS CoV-2 infection.

In some embodiments, the subject is infected with a virus. In some embodiments, the subject is infected with SARS-CoV-2.

In some embodiments, the effective amount of benzalkonium chloride is administered in the form of a pharmaceutical composition. In some embodiments, the effective amount of benzalkonium chloride is administered in the form of a pharmaceutical composition every 6 to 8 hours. In some embodiments, the effective amount of benzalkonium chloride is administered in the form of a pharmaceutical composition every 8 hours.

In some embodiments, the pharmaceutical composition is the form of an eye drop, a suspension, a gel, an ointment, an injectable solution, or a spray. In some embodiments, the pharmaceutical composition is the form of an eye drop. In some embodiments, the pharmaceutical composition is the form of a suspension. In some embodiments, the pharmaceutical composition is the form of a gel. In some embodiments, the pharmaceutical composition is the form of an ointment. In some embodiments, the pharmaceutical composition is the form of an injectable solution. In some embodiments, the pharmaceutical composition is the form of a spray.

In some embodiments, the pharmaceutical composition further comprises an effective amount of at least one additional therapeutic agent.

In some embodiments, the at least one additional therapeutic agent is chosen from anti-histamines. In some embodiments, the at least one additional therapeutic agent is chosen from pheniramine maleate, carbinoxamine maleate, S-(+)-chlorpheniramine maleate, diphenhydramine, hydroxyzine, and azelastine. In some embodiments, the at least one additional therapeutic agent is pheniramine maleate. In some embodiments, the at least one additional therapeutic agent is chosen from anti-histamines, anti-inflammatory agents, and antibiotics. In some embodiments, the at least one additional therapeutic agent is chosen from anti-inflammatory agents and antibiotics. In some embodiments, the at least one additional therapeutic agent is chosen from anti-inflammatory agents. In some embodiments, the at least one additional therapeutic agent is chosen from antibiotics.

In some embodiments, the at least one additional therapeutic agent is chosen from fluoroquinolones and $\alpha_2$-adrenergic agonists. In some embodiments, the at least one additional therapeutic agent is chosen from fluoroquinolones. In some embodiments, the at least one additional therapeutic agent is chosen from $\alpha_2$-adrenergic agonists.

In some embodiments, the at least one additional therapeutic agent is chosen from besifloxacin and brimonidine tartrate. In some embodiments, the at least one additional therapeutic agent is besifloxacin. In some embodiments, the at least one additional therapeutic agent is brimonidine tartrate.

In some embodiments, the effective amount of benzalkonium chloride is administered in the form of a pharmaceutical composition comprising 0.001% (w/v) to 0.02% (w/v) benzalkonium chloride. In some embodiments, the effective amount of benzalkonium chloride is administered in the form of a pharmaceutical composition comprising 0.004% (w/v) to 0.02% (w/v) benzalkonium chloride. In some embodiments, the effective amount of benzalkonium chloride is administered in the form of a pharmaceutical composition comprising 0.005% (w/v) to 0.02% (w/v) benzalkonium chloride.

In some embodiments, the effective amount of benzalkonium chloride is administered in the form of a pharmaceutical composition comprising 0.001% (w/v) to 0.01% (w/v) benzalkonium chloride. In some embodiments, the effective amount of benzalkonium chloride is administered in the form of a pharmaceutical composition comprising 0.004% (w/v) to 0.01% (w/v) benzalkonium chloride. In some embodiments, the effective amount of benzalkonium chloride is administered in the form of a pharmaceutical composition comprising 0.005% (w/v) to 0.01% (w/v) benzalkonium chloride.

In some embodiments, the effective amount of benzalkonium chloride is administered in the form of a pharmaceutical composition comprising 0.001% (w/v) benzalkonium chloride.

In some embodiments, the effective amount of benzalkonium chloride is administered in the form of a pharmaceutical composition comprising 0.0015% (w/v) benzalkonium chloride.

In some embodiments, the effective amount of benzalkonium chloride is administered in the form of a pharmaceutical composition comprising 0.002% (w/v) benzalkonium chloride.

In some embodiments, the effective amount of benzalkonium chloride is administered in the form of a pharmaceutical composition comprising 0.0025% (w/v) benzalkonium chloride.

In some embodiments, the effective amount of benzalkonium chloride is administered in the form of a pharmaceutical composition comprising 0.003% (w/v) benzalkonium chloride.

In some embodiments, the effective amount of benzalkonium chloride is administered in the form of a pharmaceutical composition comprising 0.0035% (w/v) benzalkonium chloride.

In some embodiments, the effective amount of benzalkonium chloride is administered in the form of a pharmaceutical composition comprising 0.004% (w/v) benzalkonium chloride.

In some embodiments, the effective amount of benzalkonium chloride is administered in the form of a pharmaceutical composition comprising 0.0045% (w/v) benzalkonium chloride.

In some embodiments, the effective amount of benzalkonium chloride is administered in the form of a pharmaceutical composition comprising 0.005% (w/v) benzalkonium chloride.

In some embodiments, the effective amount of benzalkonium chloride is administered in the form of a pharmaceutical composition comprising 0.0055% (w/v) benzalkonium chloride.

In some embodiments, the effective amount of benzalkonium chloride is administered in the form of a pharmaceutical composition comprising 0.006% (w/v) benzalkonium chloride.

In some embodiments, the effective amount of benzalkonium chloride is administered in the form of a pharmaceutical composition comprising 0.0065% (w/v) benzalkonium chloride.

In some embodiments, the effective amount of benzalkonium chloride is administered in the form of a pharmaceutical composition comprising 0.007% (w/v) benzalkonium chloride.

In some embodiments, the effective amount of benzalkonium chloride is administered in the form of a pharmaceutical composition comprising 0.0075% (w/v) benzalkonium chloride.

In some embodiments, the effective amount of benzalkonium chloride is administered in the form of a pharmaceutical composition comprising 0.008% (w/v) benzalkonium chloride.

In some embodiments, the effective amount of benzalkonium chloride is administered in the form of a pharmaceutical composition comprising 0.0085% (w/v) benzalkonium chloride.

In some embodiments, the effective amount of benzalkonium chloride is administered in the form of a pharmaceutical composition comprising 0.009% (w/v) benzalkonium chloride.

In some embodiments, the effective amount of benzalkonium chloride is administered in the form of a pharmaceutical composition comprising 0.0095% (w/v) benzalkonium chloride.

In some embodiments, the effective amount of benzalkonium chloride is administered in the form of a pharmaceutical composition comprising 0.01% (w/v) benzalkonium chloride.

In some embodiments, the effective amount of benzalkonium chloride is administered in the form of a pharmaceutical composition comprising 0.0125% (w/v) benzalkonium chloride.

In some embodiments, the effective amount of benzalkonium chloride is administered in the form of a pharmaceutical composition comprising 0.015% (w/v) benzalkonium chloride.

In some embodiments, the effective amount of benzalkonium chloride is administered in the form of a pharmaceutical composition comprising 0.0175% (w/v) benzalkonium chloride.

In some embodiments, the effective amount of benzalkonium chloride is administered in the form of a pharmaceutical composition comprising 0.02% (w/v) benzalkonium chloride.

In some embodiments, the pharmaceutical composition is chosen from Acular®, Advanced Eye Relief Dry Eye Lubricant Eye Drops, Alaway®, Alomide®, Alphagan®, AzaSite®, Azopt®, Bepreve™, Betagan®, Betoptic S®, Besivance®, Children's Alaway®, Ciloxan®, Cosopt®, Elestat®, FML®, Istalol®, Lastacaft®, Lotemax® gel (loteprednol Lotemax® SM gel (loteprednol 0.38%), Lotemax® suspension (loteprednol 0.5%), Lumify®, Lumigan®, Maxidex®, Naphcon-A®, Nevanac®, Ocuflox®, Opcon-A®, Optivar®, Pataday™, Patanol®, Polytrim®, Pred Forte®, Rescula®, Soothe Long Lasting Hydration, Timoptic®, Travatan®, Trusopt®, Xalatan®, Xibrom™, Zaditor®, Zerviate™ and Zymar®.

In some embodiments, the pharmaceutical composition is chosen from Advanced Eye Relief Dry Eye Lubricant Eye Drops, Alaway®, Children's Alaway®, Lumify®, Naphcon-A®, Opcon-A®, Soothe Long Lasting Hydration, and Zaditor®.

In some embodiments, the pharmaceutical composition is chosen from Alphagan®, Azopt®, Betagan®, Betoptic S®, Cosopt®, Istalol®, Lumigan®, Rescula®, Timoptic®, Travatan®, Trusopt®, and Xalatan®.

In some embodiments, the pharmaceutical composition is chosen from Alomide®, Bepreve™, Elestat®, Lastacaft®, Optivar®, Pataday™, Patanol®, and Zerviate™.

In some embodiments, the pharmaceutical composition is chosen from FML®, Lotemax® gel (loteprednol 0.5%), Lotemax® SM gel (loteprednol 0.38%), Lotemax® suspension (loteprednol 0.5%), Maxidex®, and Pred Forte®.

In some embodiments, the pharmaceutical composition is chosen from AzaSite®, Ciloxan®, Ocoflox®, Polytrim®, and Zymar®.

In some embodiments, the pharmaceutical composition is chosen from Acular®, Nevanac®, and Xibrom™.

In some embodiments, the pharmaceutical composition is chosen from Lumify®, Besivance®, and Opcon-A®. In some embodiments, the pharmaceutical composition is Lumify®. In some embodiments, the pharmaceutical composition is Besivance®. In some embodiments, the pharmaceutical composition is Opcon-A®.

In some embodiments, the effective amount of benzalkonium chloride is topically administered. In some embodiments, the effective amount of benzalkonium chloride is administered to at least one eye of a subject. In some embodiments, the effective amount of benzalkonium chloride is topically administered to at least one eye of a subject. In some embodiments, the effective amount of benzalkonium chloride is topically administered to one eye of a subject. In some embodiments, the effective amount of benzalkonium chloride is topically administered to both eyes of a subject.

In some embodiments, the methods comprise administering an effective amount of benzalkonium chloride in combination with an effective amount of at least one additional therapeutic agent. In some embodiments, the at least one additional therapeutic agent is chosen from anti-histamines. In some embodiments, the at least one additional therapeutic agent is chosen from pheniramine maleate, carbinoxamine maleate, S-(+)-chlorpheniramine maleate, diphenhydramine, hydroxyzine, and azelastine. In some embodiments, the at least one additional therapeutic agent is pheniramine maleate. In some embodiments, the at least one additional therapeutic agent is chosen from anti-histamines, anti-inflammatory agents, and antibiotics. In some embodiments, the at least one additional therapeutic agent is chosen from anti-inflammatory agents and antibiotics. In some embodiments, the at least one additional therapeutic agent is chosen from fluoroquinolones and $\alpha_2$-adrenergic agonists.

In some embodiments, the at least one additional therapeutic agent is chosen from besifloxacin and brimonidine tartrate. In some embodiments, the at least one additional therapeutic agent is besifloxacin. In some embodiments, the at least one additional therapeutic agent is brimonidine tartrate.

Some embodiments of the present disclosure relate to methods for reducing an intranasal SARS-CoV-2 viral load comprising administering to a subject in need thereof an effective amount of benzalkonium chloride.

In some embodiments, the effective amount of benzalkonium chloride is administered in the form of a pharmaceutical composition. In some embodiments, the effective amount of benzalkonium chloride is administered in the form of a pharmaceutical composition every 6 to 8 hours. In some embodiments, the effective amount of benzalkonium chloride is administered in the form of a pharmaceutical composition every 8 hours.

In some embodiments, the effective amount of benzalkonium chloride is administered in the form of a pharmaceutical composition comprising 0.001% (w/v) to 0.2% (w/v) benzalkonium chloride. In some embodiments, the effective amount of benzalkonium chloride is administered in the form of a pharmaceutical composition comprising 0.005% (w/v) to 0.2% (w/v) benzalkonium chloride. In some embodiments, the effective amount of benzalkonium chloride is administered in the form of a pharmaceutical composition comprising 0.005% (w/v) to 0.1% (w/v) benzalkonium chloride.

In some embodiments, the effective amount of benzalkonium chloride is administered in the form of a pharmaceutical composition comprising 0.01% (w/v) benzalkonium chloride. In some embodiments, the effective amount of benzalkonium chloride is administered in the form of a pharmaceutical composition comprising 0.02% (w/v) benzalkonium chloride.

In some embodiments, the pharmaceutical composition further comprises an effective amount of at least one additional therapeutic agent.

In some embodiments, the pharmaceutical composition is the form of a spray.

In some embodiments, the pharmaceutical composition is intranasally administered.

In some embodiments, the methods comprise administering an effective amount of benzalkonium chloride in combination with an effective amount of at least one additional therapeutic agent.

Some embodiments of the present disclosure relate to methods for treating or preventing coronavirus disease 2019 (COVID-19) comprising intranasally administering to a subject in need thereof an effective amount of benzalkonium chloride.

In some embodiments, the effective amount of benzalkonium chloride is intranasally administered in the form of a pharmaceutical composition. In some embodiments, the effective amount of benzalkonium chloride is administered in the form of a pharmaceutical composition every 6 to 8 hours. In some embodiments, the effective amount of benzalkonium chloride is administered in the form of a pharmaceutical composition every 8 hours.

In some embodiments, the effective amount of benzalkonium chloride is intranasally administered in the form of a pharmaceutical composition comprising 0.001% (w/v) to 0.2% (w/v) benzalkonium chloride. In some embodiments, the effective amount of benzalkonium chloride is intranasally administered in the form of a pharmaceutical composition comprising 0.005% (w/v) to 0.2% (w/v) benzalkonium chloride. In some embodiments, the effective amount of benzalkonium chloride is intranasally administered in the form of a pharmaceutical composition comprising 0.005% (w/v) to 0.1% (w/v) benzalkonium chloride.

In some embodiments, the effective amount of benzalkonium chloride is intranasally administered in the form of a pharmaceutical composition comprising 0.01% (w/v) benzalkonium chloride. In some embodiments, the effective amount of benzalkonium chloride is administered in the form of a pharmaceutical composition comprising 0.02% (w/v) benzalkonium chloride.

In some embodiments, the pharmaceutical composition further comprises an effective amount of at least one additional therapeutic agent.

In some embodiments, the pharmaceutical composition is the form of a spray.

In some embodiments, the methods comprise intranasally administering an effective amount of benzalkonium chloride in combination with an effective amount of at least one additional therapeutic agent.

Pharmaceutical Compositions:

In some embodiments of the present disclosure, benzalkonium chloride is administered as part of a pharmaceutical composition comprising: an effective amount of benzalkonium chloride; and at least one pharmaceutically acceptable excipient.

Pharmaceutical compositions disclosed herein may be prepared according to any known method for the manufacture of cosmetic and/or medical formulations or preparations. As will be appreciated by those of ordinary skill in the art, a number of methods are known. In some embodiments, the pharmaceutical compositions disclosed herein may be prepared by any conventional technique, such as, e.g., those described in Remington: The Science and Practice of Pharmacy, 21st edition, 2005, ed. D. B. Troy, Lippincott Williams & Wilkins, Philadelphia, and Encyclopedia of Pharmaceutical Technology, eds. J. Swarbrick and J. C. Boylan, 1988-1999, Marcel Dekker, New York.

The proportion and nature of any pharmaceutically acceptable excipient may be determined by the chosen route of administration and standard pharmaceutical practice. One of ordinary skill in the art can readily select the proper form and route of administration depending upon the disorder or condition to be treated, the stage of the disorder or condition, and other relevant circumstances. In some embodiments, the pharmaceutical composition can be administered by any convenient route. In some embodiments, the pharmaceutical composition is topically administered. In some embodiments, the pharmaceutical composition is topically administered to the ocular surface. In some embodiments, the pharmaceutical composition is topically administered to the cornea. In some embodiments, the pharmaceutical composition is instilled into the conjunctival sac.

In some embodiments, the pharmaceutical composition is in the form of an eye drop, a suspension, a gel, an ointment, an injectable solution, or a spray.

In some embodiments, the pharmaceutical composition is in any liquid form suitable for topical application. In some embodiments, the pharmaceutical composition is in the form of an eye drop. In some embodiments, the pharmaceutical composition is in the form of artificial tears. In some embodiments, the pharmaceutical composition is in the form of a contact lens adsorbent comprising a liquid carrier, such as, e.g., a cellulose ether, such as, e.g., methylcellulose.

In some embodiments, the pharmaceutical composition is in any liquid form suitable for intranasal administration. In some embodiments, the pharmaceutical composition is in the form of a nasal spray.

Except insofar as any conventional pharmaceutically acceptable excipient is incompatible with benzalkonium chloride, such as, e.g., by producing any undesirable biological effect or otherwise interacting in a deleterious manner with any other component(s) of the pharmaceutically composition, its use is contemplated to be within the scope of this disclosure. Remington: The Science and Practice of Pharmacy, 21st edition, 2005, ed. D. B. Troy, Lippincott Williams & Wilkins, Philadelphia, and Encyclopedia of Pharmaceutical Technology, eds. J. Swarbrick and J. C. Boylan, 1988-1999, Marcel Dekker, New York discloses non-limiting examples of pharmaceutically acceptable excipients, as well as known techniques for preparing and using the same.

In some embodiments, the at least one pharmaceutical excipient is chosen from humectants, tonicity agents, suspending agents, viscosity-increasing agents, wetting agents, solubilizing agents, buffering agents, antioxidants, alkalizing agents, chelating agents, stabilizers, and pharmaceutical vehicles.

In some embodiments, the suspending agents and viscosity-increasing agents are chosen from povidone K90, USP/EP, HPMC E15LV (USP), polycarbophil, and HPMC E4M USP.

In some embodiments, the wetting agents and solubilizing agents are chosen from poloxamer 407 and PS80.

In some embodiments, the buffering agents are chosen from boric acid NF and sodium borate decahydrate.

In some embodiments, the antioxidant is sodium thiosulfate pentahydrate.

In some embodiments, the alkalizing agent is sodium hydroxide NF (2N).

In some embodiments, the chelating agent is disodium EDTA, dihydrate USP/EP.

In some embodiments, the stabilizers are chosen from ascorbic acid, citric acid, sodium benzoate, calcium propionate, sodium erythorbate, sodium nitrite, calcium sorbate, potassium sorbate, BHA, BHT, EDTA, and tocopherols.

In some embodiments, the pharmaceutical vehicle is water USP/EP.

In some embodiments, the pharmaceutical composition is sterile. In some embodiments, sterility is conferred by any conventional method. In some embodiments, sterility is conferred by filtration. In some embodiments, sterility is conferred by irradiation. In some embodiments, sterility is conferred by heating. In some embodiments, sterility is conferred by conducting the manufacturing process under aseptic conditions.

EXAMPLES

The following examples are intended to be illustrative and are not meant in any way to limit the scope of the disclosure.

Abbreviations

Percent
ASTM American Society for Testing and Materials
BAK Benzalkonium chloride
DMEM Dulbecco's Modified Eagle Medium
FBS Fetal Bovine Serum
h Hour(s)
ISO International Organization for Standardization
MEM Minimal Essential Medium
mL Milliliter(s)
NCS Newborn Calf Serum
$TCID_{50}$/mL 50% tissue culture infective dose per mL

Example 1: In Vitro Antiviral Activity of Lumify®, Besivance®, and Opcon-A®, Three Benzalkonium Chloride Preserved Eye Drops, Against Severe Acute Respiratory Syndrome-Related Coronavirus 2 (SARS-CoV-2)

The in vitro antiviral activity of three 0.01% benzalkonium chloride (BAK) preserved eye drops—brimonidine tartrate ophthalmic solution, 0.025% (Lumify®), besifloxacin ophthalmic suspension 0.6% (Besivance®), and an ophthalmic solution comprising naphazoline HCl, 0.02675%, and pheniramine maleate, 0.315% (Opcon-A®)—against SARS-CoV-2 was evaluated using a Vero E6 host-cell system. Both BAK-preserved eye drop formulations demonstrated in vitro antiviral activity against SARS-CoV-2.

SARS-CoV-2 (strain USA-WA1/2020) cultures were prepared by suspending the strain in Minimal Essential Medium (MEM) with 5% heat inactivated Fetal Bovine Serum (FBS). Time kill testing of SARS-CoV-2 was conducted by multiple dosing of each test formulation at contact times representative of those recommended in the Instructions for Use of each product. All tests were conducted in triplicate and in accordance with ASTM E1052-20, suspension time-kill test for virus, standard practices. Briefly, the initial SARS-CoV-2 suspension was diluted 1:10 with the test formulations for a final concentration of $1\times10^{3.5}$-$1\times10^{4.5}$ infective units/mL. Following the required contact time, test solutions were neutralized with 10 mL MEM with 10% Newborn Calf Serum, serially diluted, and inoculated onto the Vero E6 host-cell system. Appropriate controls and test samples were incubated with the Vero cells at 36° C.±2° C. After 4 to 9 days, the presence of residual viable virus was scored. Viral titers, expressed as 50% tissue culture infective dose per mL ($TCID_{50}$/mL), were calculated using the Spearman-Karber computation, and $\log_{10}$ reductions were determined (Table 1).

$Log_{10}$ reductions for brimonidine tartrate 0.025% were ≥1.80, ≥2.14, and ≥2.02 at 8-hour, 24-hour, and 72-hour contact times, respectively. $Log_{10}$ reductions for besifloxacin were ≥1.95 at the 24-hour and ≥2.56 at the 72-hour contact times. Logic) reductions for naphazoline and pheniramine maleate were ≥2.14 at the 24-hour and >2.02 at the 72-hour contact times. These results indicate complete inactivation of SARS-CoV-2 at all contact times.

TABLE 1

$Log_{10}$ Reductions (SARS-CoV-2)

| | 0.01% BAK-Containing Ophthalmic Formulations | | |
|---|---|---|---|
| Contact Time (h) | Lumify ® | Besivance ® | Opcon-A ® |
| 8 | ≥1.80 | — | |
| 24 | ≥2.14 | ≥1.95 | ≥2.14 |
| 72 | ≥2.02 | ≥2.56 | ≥2.02 |

Example 2: SARS-CoV-2 Virucidal Efficacy Test for BAK-Preserved Solutions

The in vitro antiviral activity of five BAK-preserved ophthalmic solutions—Opcon-A (0.01% BAK), Advanced Eye Relief, (0.01% BAK) Lumify (0.01% BAK), Soothe Maximum Hydration (0.005% BAK), and Advanced Eye Relief Eye Wash Eye Irrigating Solution (0.01% BAK)—against SARS-CoV-2 was evaluated using a Vero E6 host-cell system. All five BAK-preserved eye drop formulations demonstrated in vitro antiviral activity against SARS-CoV-2 after a contact time of 7 days.

TABLE 2

$Log_{10}$ Reductions After 7-Day Contact Time (SARS-CoV-2)

| Test Substance | Replicate | $Log_{10}$ Reduction |
|---|---|---|
| Opcon-A | Rep 1 | ≥3.24 |
| | Rep 2 | ≥3.24 |
| | Rep 3 | ≥3.24 |
| Advanced Eye Relief | Rep 1 | ≥4.24 |
| | Rep 2 | ≥4.24 |
| | Rep 3 | ≥4.24 |
| Lumify | Rep 1 | ≥4.24 |
| | Rep 2 | ≥4.24 |
| | Rep 3 | ≥4.24 |
| Soothe Maximum Hydration | Rep 1 | ≥3.24 |
| | Rep 2 | ≥3.24 |
| | Rep 3 | ≥3.24 |
| Advanced Eye Relief Eye Wash Eye Irrigating Solution | Rep 1 | ≥4.24 |
| | Rep 2 | ≥4.24 |
| | Rep 3 | ≥4.24 |

SARS-CoV-2 (strain CDC 200300592) cultures were prepared by suspending the strain in Minimal Essential Medium (MEM) with 2% Newborn Calf Serum (NCS). Time kill testing of SARS-CoV-2 was conducted by multiple dosing of each test formulation at specified contact times. All tests were conducted in triplicate and in accordance with ASTM E1052-20, suspension time-kill test for virus, standard practices. Briefly, the initial SARS-CoV-2 suspension was diluted 1:100 with the test formulations. After 7 days, test solutions were neutralized with MEM with 10% NCS, serially diluted, and inoculated onto the Vero E6 host-cell system. Appropriate controls and test samples were incubated with the Vero cells, and the presence of residual viable virus was scored.

Viral titers, expressed as 50% tissue culture infective dose per mL ($TCID_{50}$/mL), were determined using the Spearman-Karber computation based on a sample inoculum of mL, and $\log_{10}$ reductions were determined (Table 2).

Example 3: Adenovirus Type 5 (ADV-5) Virucidal Efficacy Test for BAK-Preserved Solutions Adenoviral conjunctivitis is one of the most common eye infections worldwide. The in vitro antiviral activity of five BAK-preserved ophthalmic solutions—Opcon-A (0.01% BAK), Advanced Eye Relief, (0.01% BAK) Lumify (0.01% BAK), Soothe Maximum Hydration (0.005% BAK), and Advanced Eye Relief Eye Wash Eye Irrigating Solution (0.01% BAK)—against an adenovirus, ADV-5, was evaluated using a A549 host-cell system (ATCC CCL-185). All five BAK-preserved eye drop formulations demonstrated in vitro antiviral activity against ADV-5 after a contact time of 7 days.

ADV-5 (strain Adenoid 75, ATCC VR-5) cultures were prepared by suspending the strain in Minimal Essential Medium (MEM) with 2% FBS. Time kill testing of ADV-5 was conducted by multiple dosing of each test formulation at specified contact times. All tests were conducted in triplicate and in accordance with ASTM E1052-20, suspension time-kill test for virus, standard practices. Briefly, the initial ADV-5 suspension was diluted 1:100 with the test formulations. After 7 days, test solutions were neutralized with Dulbecco's Modified Eagle Medium (DMEM) with 10% FBS, serially diluted, and inoculated onto the A549 host-cell system. Appropriate controls and test samples were incubated with the A549 cells, and the presence of residual viable virus was scored.

Viral titers, expressed as 50% tissue culture infective dose per mL ($TCID_{50}$/mL), were determined using the Spearman-Karber computation based on a sample inoculum of mL, and $log_{10}$ reductions were determined (Table 3).

TABLE 3

$Log_{10}$ Reductions After 7-Day Contact Time (ADV-5)

| Test Substance | Replicate | $Log_{10}$ Reduction |
|---|---|---|
| Opcon-A | Rep 1 | ≥3.18 |
| | Rep 2 | ≥3.18 |
| | Rep 3 | ≥3.18 |
| Advanced Eye Relief | Rep 1 | ≥3.18 |
| | Rep 2 | ≥3.18 |
| | Rep 3 | ≥3.18 |
| Lumify | Rep 1 | ≥3.18 |
| | Rep 2 | ≥3.18 |
| | Rep 3 | ≥3.18 |
| Soothe Maximum Hydration | Rep 1 | 3.09 |
| | Rep 2 | ≥3.18 |
| | Rep 3 | 3.42 |
| Advanced Eye Relief Eye Wash Eye Irrigating Solution | Rep 1 | ≥3.18 |
| | Rep 2 | ≥3.18 |
| | Rep 3 | ≥3.18 |

Example 4: Virucidal Effectiveness Under Benzalkonium Chloride (BAK) Preserved Eye Drop Instruction for Use Conditions The virucidal effectiveness of three 0.01% benzalkonium chloride (BAK) preserved eye drops—brimonidine tartrate ophthalmic solution, 0.025% (Lumify®), besifloxacin ophthalmic suspension 0.6% (Besivance®), and an ophthalmic solution comprising naphazoline HCl, 0.02675%, and pheniramine maleate, 0.315% (Opcon-A®)—against SARS-CoV-2 was measured following principles outlined in ISO 14729:2001/Amd. 1:2010 and ASTM test method E1052-20. To simulate direct instillation and maximum dose on the eye based on instructions for use in vitro, one drop of Besivance® was applied every 8 hours for up to 24 hours (maximum 3 drops); a maximum of one drop of Lumify® was applied every 6-8 hours for up to 24 hours (maximum 4 drops); and one drop of Opcon-A® was applied every 6-8 hours for up to 24 hours (maximum 4 drops).

Approximately 1×10 7 infective units/mL of SARS-CoV-2 (strain USA-WA1/2020; source: BEI Resources, NR-52281) cultures were employed in the assay, using a consistent test solution: viral inoculum ratio to ensure conformance with the ASTM method. $Log_{10}$ reductions were measured after 2-minute, 5-minute, 10-minute, 15-minute, 30-minute, 8-hour, and 24-hour contact times (Tables 4-9). These results indicate in vitro virucidal inactivation of SARS-CoV-2 after 1-hour, 8-hour, and 24-hour contact times for Besivance®, after 2-minute, 5-minute, 10-minute, 15-minute, 30-minute, 8-hour, and 24-hour contact times for Opcon-A®, and after 1-hour, 8-hour, and 24-hour contact times for Lumify®.

TABLE 4

$Log_{10}$ Reductions for Besivance ® (Up to 60-Minute Contact Time)

| Contact Time | Replicate | Initial Load ($Log_{10}TCID_{50}$) | Output Load ($Log_{10}TCID_{50}$) | $Log_{10}$ Reduction |
|---|---|---|---|---|
| 2 minutes | 1 | 5.91 | 4.82 | 1.08 |
| | 2 | 5.91 | 4.95 | 0.95 |
| | 3 | 5.91 | 4.70 | 1.20 |
| 5 minutes | 1 | 5.91 | 4.70 | 1.20 |
| | 2 | 5.91 | 4.95 | 0.95 |
| | 3 | 5.91 | 4.70 | 1.20 |
| 10 minutes | 1 | 5.91 | 4.57 | 1.33 |
| | 2 | 5.91 | 4.32 | 1.58 |
| | 3 | 5.91 | 4.20 | 1.70 |
| 15 minutes | 1 | 5.91 | 4.20 | 1.70 |
| | 2 | 5.91 | 4.32 | 1.58 |
| | 3 | 5.91 | 3.95 | 1.95 |
| 30 minutes | 1 | 5.91 | 3.07 | 2.83 |
| | 2 | 5.91 | 2.61 | 3.29 |
| | 3 | 5.91 | 2.77 | 3.13 |
| 60 minutes | 1 | 5.91 | 1.61 | 4.29 |
| | 2 | 5.91 | 1.61 | 4.29 |
| | 3 | 5.91 | 1.94 | 3.96 |

TABLE 5

$Log_{10}$ Reductions for Besivance ® (8-Hour, 24-Hour Contact Time)

| Contact Time | Dosing Regimen | Replicate | *Initial Load ($Log_{10}TCID_{50}$) | Output Load ($Log_{10}TCID_{50}$) | **$Log_{10}$ Reduction |
|---|---|---|---|---|---|
| 8 hours | T = 0 | 1 | 5.30 | ≤2.22 | ≥3.08 |
| | T = 4 | 2 | 5.30 | ≤2.22 | ≥3.08 |
| | | 3 | 5.30 | ≤2.22 | ≥3.08 |
| 24 hours | T = 0 | 1 | 5.52 | ≤2.24 | ≥3.28 |
| | T = 4 | 2 | 5.52 | ≤2.24 | ≥3.28 |
| | T = 8 | 3 | 5.52 | ≤2.24 | ≥3.28 |

*Average Virus Recovery Control (VRC) Initial Load

**Denotes a complete inactivation of virus under these test conditions

TABLE 6

| Log$_{10}$ Reductions for Opcon-A ® (Up to 60-Minute Contact Time) | | | | |
|---|---|---|---|---|
| Contact Time | Replicate | Initial Load ($Log_{10}TCID_{50}$) | Output Load ($Log_{10}TCID_{50}$) | $Log_{10}$ Reduction |
| 2 minutes | 1 | 5.10 | ≤1.23 | ≥3.87 |
| | 2 | 5.10 | ≤1.23 | ≥3.87 |
| | 3 | 5.10 | ≤1.23 | ≥3.87 |
| 5 minutes | 1 | 5.10 | ≤1.23 | ≥3.87 |
| | 2 | 5.10 | ≤1.23 | ≥3.87 |
| | 3 | 5.10 | ≤1.23 | ≥3.87 |
| 10 minutes | 1 | 5.10 | ≤1.23 | ≥3.87 |
| | 2 | 5.10 | ≤1.23 | ≥3.87 |
| | 3 | 5.10 | ≤1.23 | ≥3.87 |
| 15 minutes | 1 | 5.10 | ≤1.23 | ≥3.87 |

TABLE 6-continued

| Log$_{10}$ Reductions for Opcon-A ® (Up to 60-Minute Contact Time) | | | | |
|---|---|---|---|---|
| Contact Time | Replicate | Initial Load ($Log_{10}TCID_{50}$) | Output Load ($Log_{10}TCID_{50}$) | $Log_{10}$ Reduction |
| | 2 | 5.10 | ≤1.23 | ≥3.87 |
| | 3 | 5.10 | ≤1.23 | ≥3.87 |
| 30 minutes | 1 | 5.10 | ≤1.23 | ≥3.87 |
| | 2 | 5.10 | ≤1.23 | ≥3.87 |
| | 3 | 5.10 | ≤1.23 | ≥3.87 |
| 60 minutes | 1 | 5.10 | ≤1.23 | ≥3.87 |
| | 2 | 5.10 | ≤1.23 | ≥3.87 |
| | 3 | 5.10 | ≤1.23 | ≥3.87 |

TABLE 7

| Log$_{10}$ Reductions for Opcon-A ® (8-Hour, 24-Hour Contact Time) | | | | | |
|---|---|---|---|---|---|
| Contact Time | Dosing Regimen | Replicate | *Initial Load ($Log_{10}TCID_{50}$) | Output Load ($Log_{10}TCID_{50}$) | **$Log_{10}$ Reduction |
| 8 hours | T = 0 | 1 | 5.64 | ≤2.26 | ≥3.37 |
| | T = 4 | 2 | 5.64 | ≤2.26 | ≥3.37 |
| | | 3 | 5.64 | ≤2.26 | ≥3.37 |
| 24 hours | T = 0 | 1 | 5.45 | ≤2.33 | ≥3.12 |
| | T = 4 | 2 | 5.45 | ≤2.33 | ≥3.12 |
| | T = 8 | 3 | 5.45 | ≤2.33 | ≥3.37 |
| | T = 12 | | | | |

*Average Virus Recovery Control (VRC) Initial Load

**Denotes a complete inactivation of virus under these test conditions

TABLE 8

| Log$_{10}$ Reductions for Lumify ® (Up to 60-Minute Contact Time) | | | | |
|---|---|---|---|---|
| Contact Time | Replicate | Initial Load ($Log_{10}TCID_{50}$) | Output Load ($Log_{10}TCID_{50}$) | $Log_{10}$ Reduction |
| 2 minutes | 1 | 5.23 | 4.85 | 0.38 |
| | 2 | 5.23 | 4.85 | 0.38 |
| | 3 | 5.23 | 5.10 | 0.13 |
| 5 minutes | 1 | 5.23 | 3.23 | 2.00 |
| | 2 | 5.23 | 3.48 | 1.75 |
| | 3 | 5.23 | 3.35 | 1.88 |
| 10 minutes | 1 | 5.23 | 2.65 | 2.58 |
| | 2 | 5.23 | 2.50 | 2.73 |
| | 3 | 5.23 | 2.83 | 2.40 |
| 15 minutes | 1 | 5.23 | 2.50 | 2.73 |
| | 2 | 5.23 | 2.72 | 2.51 |
| | 3 | 5.23 | 2.64 | 2.59 |
| 30 minutes | 1 | 5.23 | 2.35 | 2.58 |
| | 2 | 5.23 | 1.97 | 3.26 |
| | 3 | 5.23 | 1.97 | 3.26 |
| 60 minutes | 1 | 5.23 | 1.64 | 3.59 |
| | 2 | 5.23 | 1.64 | 3.59 |
| | 3 | 5.23 | 0.91 | 4.32 |

TABLE 9

| Log$_{10}$ Reductions for Lumify ® (8-Hour, 24-Hour Contact Time) | | | | | |
|---|---|---|---|---|---|
| Contact Time | Dosing Regimen | Replicate | *Initial Load ($Log_{10}TCID_{50}$) | Output Load ($Log_{10}TCID_{50}$) | **$Log_{10}$ Reduction |
| 8 hours | T = 0 | 1 | 5.64 | ≤1.26 | ≥4.37 |
| | T = 4 | 2 | 5.64 | ≤1.26 | ≥4.37 |
| | | 3 | 5.64 | ≤1.26 | ≥4.37 |

TABLE 9-continued

| Log$_{10}$ Reductions for Lumify ® (8-Hour, 24-Hour Contact Time) | | | | | |
|---|---|---|---|---|---|
| Contact Time | Dosing Regimen | Replicate | *Initial Load (Log$_{10}$TCID$_{50}$) | Output Load (Log$_{10}$TCID$_{50}$) | **Log$_{10}$ Reduction |
| 24 hours | T = 0 | 1 | 5.45 | ≤1.33 | ≥4.12 |
| | T = 4 | 2 | 5.45 | ≤1.33 | ≥4.12 |
| | T = 8 | 3 | 5.45 | ≤1.33 | ≥4.12 |
| | T = 12 | | | | |

*Average Virus Recovery Control (VRC) Initial Load
**Denotes a complete inactivation of virus under these test conditions The foregoing disclosure has been described in some detail by way of illustration and example, for purposes of clarity and understanding. Therefore, it is to be understood that the above description is intended to be illustrative and not restrictive. The scope of the disclosure should, therefore, be determined not with reference to the above description, but should instead be determined with reference to the following appended claims, along with the full scope of equivalents to which such claims are entitled.

What is claimed is:

1. A method for treating at least one ocular manifestation of coronavirus disease 2019 (COVID-19) comprising administering to a subject in need thereof a pharmaceutical composition comprising an effective amount of benzalkonium chloride, pheniramine maleate, and naphazoline HCl.

2. The method of claim 1, wherein the pharmaceutical composition comprises 0.001% (w/v) to 0.02% (w/v) benzalkonium chloride.

3. The method of claim 1, wherein the pharmaceutical composition comprises 0.01% (w/v) benzalkonium chloride.

4. The method of claim 1, wherein the pharmaceutical composition is the form of an eye drop, a suspension, a gel, an ointment, an injectable solution, or a spray.

5. The method of claim 1, wherein the pharmaceutical composition is topically administered.

6. The method of claim 1, wherein the pharmaceutical composition is administered to at least one eye of the subject.

7. The method of claim 1, wherein treating at least one ocular manifestation of COVID-19 comprises treating at least one disease or condition chosen from eye redness, conjunctivitis, keratoconjunctivitis, dry eye disease, blurred vision, conjunctival hyperaemia, ocular irritation, foreign body sensation, epiphora, eyelid edema, and chemosis.

8. The method of claim 1, wherein treating at least one ocular manifestation of COVID-19 comprises treating conjunctivitis.

9. The method of claim 1, wherein treating at least one ocular manifestation of COVID-19 comprises improving visual acuity.

10. The method of claim 1, wherein treating at least one ocular manifestation of COVID-19 comprises reducing eye redness, ocular irritation, or foreign body sensation.

11. A method for reducing a risk of SARS-COV-2 ocular transmission comprising administering to a subject in need thereof a pharmaceutical composition comprising an effective amount of benzalkonium chloride, pheniramine maleate, and naphazoline HCl.

12. The method of claim 11, wherein the pharmaceutical composition comprises 0.001% (w/v) to 0.02% (w/v) benzalkonium chloride.

13. The method of claim 11, wherein the pharmaceutical composition comprises 0.01% (w/v) benzalkonium chloride.

14. The method of claim 11, wherein the pharmaceutical composition is the form of an eye drop, a suspension, a gel, an ointment, an injectable solution, or a spray.

15. The method of claim 11, wherein the pharmaceutical composition is topically administered.

16. The method of claim 11, wherein the pharmaceutical composition is administered to at least one eye of the subject.

17. A method for preventing coronavirus disease 2019 (COVID-19) comprising administering to a subject in need thereof a pharmaceutical composition comprising an effective amount of benzalkonium chloride, pheniramine maleate, and naphazoline HCl.

18. The method of claim 17, wherein the pharmaceutical composition comprises 0.001% (w/v) to 0.02% (w/v) benzalkonium chloride.

19. The method of claim 17, wherein the pharmaceutical composition comprises 0.01% (w/v) benzalkonium chloride.

20. The method of claim 17, wherein the pharmaceutical composition is the form of an eye drop, a suspension, a gel, an ointment, an injectable solution, or a spray.

21. The method of claim 17, wherein the pharmaceutical composition is topically administered.

22. The method of claim 17, wherein the pharmaceutical composition is administered to at least one eye of the subject.

23. A method for reducing an ocular SARS-COV-2 viral load comprising administering to a subject in need thereof a pharmaceutical composition comprising an effective amount of benzalkonium chloride, pheniramine maleate, and naphazoline HCl.

24. The method of claim 23, wherein the pharmaceutical composition comprises 0.001% (w/v) to 0.02% (w/v) benzalkonium chloride.

25. The method of claim 23, wherein the pharmaceutical composition comprises 0.01% (w/v) benzalkonium chloride.

26. The method of claim 23, wherein the pharmaceutical composition is the form of an eye drop, a suspension, a gel, an ointment, an injectable solution, or a spray.

27. The method of claim 23, wherein the pharmaceutical composition is topically administered.

28. The method of claim 23, wherein the pharmaceutical composition is administered to at least one eye of the subject.

29. A method for reducing an intranasal SARS-COV-2 viral load comprising administering to a subject in need thereof a pharmaceutical composition comprising an effective amount of benzalkonium chloride, pheniramine maleate, and naphazoline HCl.

30. The method of claim 29, wherein the pharmaceutical composition comprises 0.001% (w/v) to 0.2% (w/v) benzalkonium chloride.

31. The method of claim 29, wherein the pharmaceutical composition comprises 0.005% (w/v) to 0.2% (w/v) benzalkonium chloride.

32. The method of claim 29, wherein the pharmaceutical composition comprises 0.005% (w/v) to 0.1% (w/v) benzalkonium chloride.

33. The method of claim 29, wherein the pharmaceutical composition comprises 0.01% (w/v) benzalkonium chloride.

34. The method of 29, wherein the pharmaceutical composition is the form of a spray.

35. A method for treating or preventing coronavirus disease 2019 (COVID-19) comprising intranasally administering to a subject in need thereof a pharmaceutical composition comprising an effective amount of benzalkonium chloride, pheniramine maleate, and naphazoline HCl.

36. The method of claim 35, wherein the pharmaceutical composition comprises 0.001% (w/v) to 0.2% (w/v) benzalkonium chloride.

37. The method of claim 35, wherein the pharmaceutical composition comprises 0.005% (w/v) to 0.2% (w/v) benzalkonium chloride.

38. The method of claim 35, wherein the pharmaceutical composition comprises 0.005% (w/v) to 0.1% (w/v) benzalkonium chloride.

39. The method of claim 35, wherein the pharmaceutical composition comprises 0.01% (w/v) benzalkonium chloride.

40. The method of claim 35, wherein the pharmaceutical composition is the form of a spray.

* * * * *